US010415064B2

(12) United States Patent
Nicaud et al.

(10) Patent No.: US 10,415,064 B2
(45) Date of Patent: Sep. 17, 2019

(54) MUTANT YEASTS CAPABLE OF PRODUCING AN UNUSUAL FATTY ACID

(71) Applicants: INSTITUT NATIONAL DE LA RECHERCHE AGRONOMIQUE, Paris (FR); CENTRE NATIONAL DE LA RECHERCHE SCIENTIFIQUE, Paris (FR); INSTITUT NATIONAL DES SCIENCES APPLIQUEES DE TOULOUSE, Toulouse (FR)

(72) Inventors: Jean-Marc Nicaud, Trappes (FR); Alain Marty, Saint Pierre de Lages (FR); Athanasios Beopoulos, Paris (FR); Jonathan Verbeke, Antony (FR); Florence Bordes, Gaure (FR); Marie Guicherd, Toulouse (FR)

(73) Assignees: Institut National de la Recherche Agronomique, Paris (FR); Centre National de la Recherche Scientifique, Paris (FR); Institut National des Sciences Appliquees de Toulouse, Toulouse (FR)

( * ) Notice: Subject to any disclaimer, the term of this patent is extended or adjusted under 35 U.S.C. 154(b) by 0 days.

(21) Appl. No.: 14/888,605

(22) PCT Filed: Apr. 30, 2014

(86) PCT No.: PCT/IB2014/061116
§ 371 (c)(1),
(2) Date: Nov. 2, 2015

(87) PCT Pub. No.: WO2014/178014
PCT Pub. Date: Nov. 6, 2014

(65) Prior Publication Data
US 2016/0097066 A1   Apr. 7, 2016

(30) Foreign Application Priority Data
May 2, 2013 (FR) ...................... 13 54062

(51) Int. Cl.
| C12N 15/63 | (2006.01) |
| C12N 15/09 | (2006.01) |
| C12N 15/52 | (2006.01) |
| C12N 1/19  | (2006.01) |
| C12P 7/64  | (2006.01) |
| C12N 9/02  | (2006.01) |
| C12N 15/62 | (2006.01) |
| C12N 15/81 | (2006.01) |

(52) U.S. Cl.
CPC .......... *C12P 7/6409* (2013.01); *C12N 9/0071* (2013.01); *C12N 9/0073* (2013.01); *C12N 15/52* (2013.01); *C12N 15/62* (2013.01); *C12N 15/815* (2013.01); *C12P 7/6463* (2013.01)

(58) Field of Classification Search
None
See application file for complete search history.

(56) References Cited

U.S. PATENT DOCUMENTS

| 8,597,931 B2 | 12/2013 | Nicaud et al. |
| 8,748,129 B2 | 6/2014 | Nicaud et al. |
| 2010/0041115 A1 | 2/2010 | Nicaud et al. |
| 2011/0223641 A1* | 9/2011 | Stephanopoulos .... C12N 9/001 435/134 |
| 2012/0226059 A1 | 9/2012 | Faure et al. |
| 2013/0149754 A1 | 6/2013 | Dulermo et al. |
| 2016/0145599 A1 | 5/2016 | Nicaud et al. |

FOREIGN PATENT DOCUMENTS

| WO | WO 2006/064131 A1 | 6/2006 |
| WO | WO 2007/147256 | 12/2007 |
| WO | WO 2010/004141 A2 | 1/2010 |
| WO | WO 2011/008232 | 1/2011 |
| WO | WO 2011064393 A1 * | 6/2011 | ............... C12N 9/88 |
| WO | WO 2012/001144 A1 | 1/2012 |
| WO | WO 2014/178014 A1 | 6/2014 |

OTHER PUBLICATIONS

Beopoulos et al., "Metabolic engineering for ricinoleic acid production in the oleaginous yeast *Yarrowia lipolytica*", Appl. Microbiol. Biotechnol. 98:251-262, published online Oct. 2013.*
Zhou et al., Cell Mol Life Sci 63:2260-2290, 2006.*
Kozak, M., Gene 234:187-208, 1999.*
Beopoulos et al., Appl. Microbiol. Biotechnol. 98:251-262, 2013.*
Biryukova et al., Microbiology 78:154-159, 2009.*
Damude et al., PNAS 103:9446-9451, 2006 (Year: 2006).*
Marbach et al., J. Biotechnol. 157:82-88, 2012 (Year: 2012).*
Meesapyodsuk et al., "An Oleate Hydroxylase from the Fungus *Claviceps purpurea*: Cloning, Functional Analysis, and Expression in *Arabidopsis*", Plant Physiology, Jul. 2008, vol. 147, pp. 1325-1333 (Year: 2008).*
International Search Report & Written Opinion, International Application No. PCT/IB2014/06116, dated Aug. 1, 2014, in French, 18 pages, includes ISR in English.
Beopoulos et al., "Control of lipid accumulation in the yeast *Yarrowia lipolytica*," Applied & Environmental Microbiology 74(24):7779-7789, Dec. 2008.
Beopoulos et al., "Yarrowia lipolytica as a model for bio-oil production," Progress in Lipid Research 48:375-387, 2009.
Broun et al., "Catalytic plasticity of fatty acid modification enzymes underlying chemical diversity of plant lipids," Science 282:1315-1317, Nov. 13, 1998.

(Continued)

*Primary Examiner* — David Steadman
(74) *Attorney, Agent, or Firm* — Morgan, Lewis & Bockius LLP

(57) ABSTRACT

The present invention relates to a method for obtaining a mutant strain of oleaginous yeast which is useful as a template strain of yeast for obtaining other mutant strains of oleaginous yeast which are capable of producing an unusual fatty acid. The present invention also relates to the mutant strains of yeast obtained by said method.

16 Claims, 13 Drawing Sheets

Figure 2:
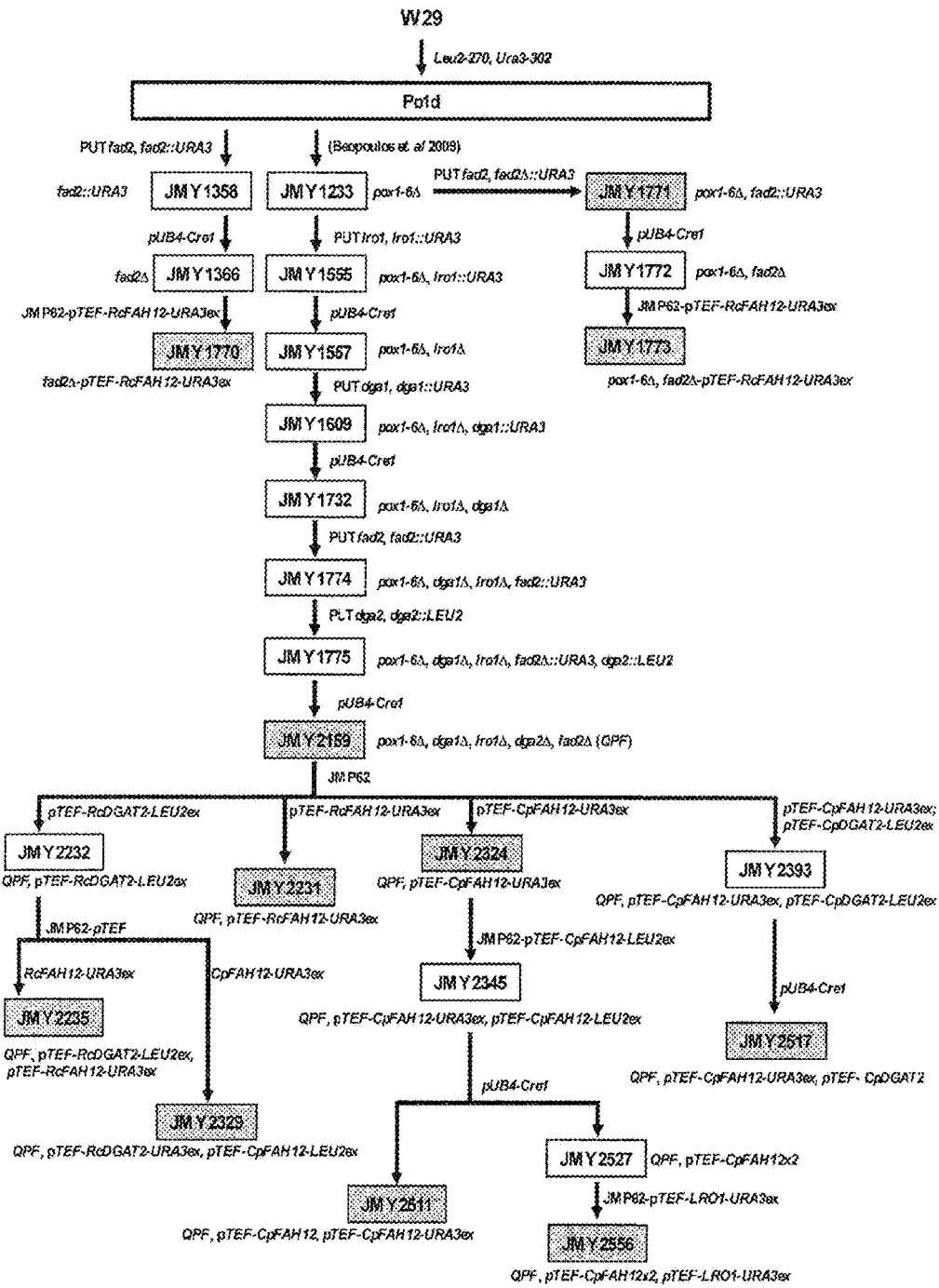

Specification includes a Sequence Listing.

(56) References Cited

OTHER PUBLICATIONS

Einerhand et al., "The upstream region of the FOX3 gene encoding peroxisomal 3-oxoacyl-coenzyme A thiolase in *Saccharomyces cerevisiae* contains ABF1- and replication protein A-binding sites that participate in its regulation by glucose repression," Mol. Cell. Biol. 15(6):3405-3414, 1995.

Haddouche et al., "Engineering polyhydroxyalkanoate content and monomer composition in the oleaginous yeast *Yarrowia lipolytica* by modifying the ß-oxidation multifunctional protein," Appl. Microbiol. Biotechnology 91:1327-1340, 2011.

Holic et al., "Engineered high content of ricinoleic acid in fusion yeast *Schizosaccharomyces pombe*," Appl. Microbiol. Biotechnology 95:179-187, 2012.

Karatay et al., "Improving the lipid accumulation properties of the yeast cells for biodiesel production using molasses," Bioresource Technology 101:7988-7990, 2010.

Meesapyodsuk et al., "An oleate hydroxylase from the fungus *Claviceps purpurea*: Cloning, functional analysis, and expression in *Arabidopsis*," Plant Physiology 147:1325-1333, 2008.

van Erp et al., "Castor phospholipid:Diacylglycerol acyltransferase facilitates efficient metabolism of hydroxy fatty acids in transgenic *Arabidopsis*," Plant Physiology 155:683-693, 2011.

Bafor et al. (1991) "Ricinoleic acid biosynthesis and triacylglycerol assembly in microsomal preparations from developing castor-bean (*Ricinus communis*) endosperm," Biochem J. 280:507-514.

Beopoulos et al. (Aug. 2, 2011) "Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts," Appl Microbiol Biotechnol. 93:1523-1537.

Broadwater et al. (2002) "Desaturation and hydroxylation. Residues 148 and 324 of *Arabidopsis* FAD2, in addition to substrate chain length, exert a major influence in partitioning of catalytic specificity," J Biol Chem. 277:15613-15620.

Broun et al. (1997) "Accumulation of ricinoleic, lesquerolic, and densipolic acids in seeds of transgenic *Arabidopsis* plants that express a fatty acyl hydroxylase cDNA from castor bean," Plant Physiol. 113:933-942.

Browse et al. (1986) "Fatty acid composition of leaf lipids determined after combined digestion and fatty acid methyl ester formation from fresh tissue," Anal Biochem. 152:141-145.

Burgal et al. (2008) "Metabolic engineering of hydroxy fatty acid production in plants: RcDGAT2 drives dramatic increases in ricinoleate levels in seed oil," Plant Biotechnol J. 6:819-831.

Dear et al. (1991) "A sequence assembly and editing program for efficient management of large projects," Nucleic Acids Res. 19:3907-3911.

Dulermo et al. (May 23, 2011) "Involvement of the G3P shuttle and β-oxidation pathway in the control of TAG synthesis and lipid accumulation in Yarrowia lipolytica," Metab Eng. 13:482-491.

Fickers et al. (2003) "New disruption cassettes for rapid gene disruption and marker rescue in the yeast *Yarrowia lipolytica*," J Microbiol Methods. 55:727-737.

Folch et al. (1957) "A simple method for the isolation and purification of total lipides from animal tissues," J Biol Chem. 226:497-509.

Gaillardin et al. (1987) "LEU2 directed expression of beta-galactosidase activity and phleomycin resistance in Yarrowia lipolytica," Curr Genet. 11:369-375.

GenBank Database [online] (Jan. 1, 2010) "Ricinus communis oleate 12-hydroxylase (FAH12) mRNA, complete cds," Accession No. EU523112. National Center for Biotechnology Information. Accessible on the Internet at URL: http://www.ncbi.nlm.nih.gov/nuccore/187940238. [Last Accessed Mar. 9, 2016].

GenBank Database [online] (Jul. 20, 2008) "Claviceps purpurea fatty acid hydroxylase (FAH) mRNA, complete cds," Accession No. EU661785. National Center for Biotechnology Information. Accessible on the Internet at URL: http://www.ncbi.nlm.nih.gov/nuccore/194271137. [Last Accessed Mar. 9, 2016].

Genolevures Database [online] "YALI0B10153g," Laboratoire Bordelais de Recherche en Informatique. Accessible on the Internet at URL: http://www.genolevures.org/elt/YALI/YALI0B10153g. [Last Accessed Mar. 9, 2016].

Genolevures Database [online] "YALI0C23859g," Laboratoire Bordelais de Recherche en Informatique. Accessible on the Internet at URL: http://www.genolevures.org/elt/YALI/YALI0C23859g. [Last Accessed Mar. 9, 2016].

Genolevures Database [online] "YALI0D07986g," Laboratoire Bordelais de Recherche en Informatique. Accessible on the Internet at URL: http://www.genolevures.org/elt/YALI/YALI0D07986g. [Last Accessed Mar. 9, 2016].

Genolevures Database [online] "YALI0D24750g," Laboratoire Bordelais de Recherche en Informatique. Accessible on the Internet at URL: http://www.genolevures.org/elt/YALI/YALI0D24750g. [Last Accessed Mar. 9, 2016].

Genolevures Database [online] "YALI0E06567g," Laboratoire Bordelais de Recherche en Informatique. Accessible on the Internet at URL: http://www.genolevures.org/elt/YALI/YALI0E06567g. [Last Accessed Mar. 9, 2016].

Genolevures Database [online] "YALI0E16797g," Laboratoire Bordelais de Recherche en Informatique. Accessible on the Internet at URL: http://www.genolevures.org/elt/YALI/YALI0E16797g. [Last Accessed Mar. 9, 2016].

Genolevures Database [online] "YALI0E27654g," Laboratoire Bordelais de Recherche en Informatique. Accessible on the Internet at URL: http://www.genolevures.org/elt/YALI/YALI0E27654g. [Last Accessed Mar. 9, 2016].

Genolevures Database [online] "YALI0E32769g," Laboratoire Bordelais de Recherche en Informatique. Accessible on the Internet at URL: http://www.genolevures.org/elt/YALI/YALI0E32769g. [Last Accessed Mar. 9, 2016].

Genolevures Database [online] "YALI0E32835g," Laboratoire Bordelais de Recherche en Informatique. Accessible on the Internet at URL: http://www.genolevures.org/elt/YALI/YALI0E32835g. [Last Accessed Mar. 9, 2016].

Genolevures Database [online] "YALI0F10857g," Laboratoire Bordelais de Recherche en Informatique. Accessible on the Internet at URL: http://www.genolevures.org/elt/YALI/YALI0F10857g. [Last Accessed Mar. 9, 2016].

Lee et al. (1998) "Identification of non-heme diiron proteins that catalyze triple bond and epoxy group formation," Science. 280:915-918.

Lu et al. (2006) "A high-throughput screen for genes from castor that boost hydroxy fatty acid accumulation in seed oils of transgenic *Arabidopsis*," Plant J. 45:847-856.

Luo et al. (2000) "Purification and characterization of the recombinant form of Acyl CoA oxidase 3 from the yeast *Yarrowia lipolytica*," Arch Biochem Biophys. 384:1-8.

Luo et al. (2002) "The acyl-CoA oxidases from the yeast *Yarrowia lipolytica*: characterization of Aox2p," Arch Biochem Biophys. 407:32-38.

Mavraganis et al. (2010) "Type II diacylglycerol acyltransferase from Claviceps purpurea with ricinoleic acid, a hydroxyl fatty acid of industrial importance, as preferred substrate," Appl Environ Microbiol. 76:1135-1142.

Mlickova et al. (2004) "Lipid accumulation, lipid body formation, and acyl coenzyme A oxidases of the yeast *Yarrowia lipolytica*," Appl Environ Microbiol. 70:3918-3924.

Muller et al. (1998) "Comparison of expression systems in the yeasts *Saccharomyces cerevisiae, Hansenula polymorpha, Klyveromyces lactis, Schizosaccharomyces pombe* and *Yarrowia lipolytica*. Cloning of two novel promoters from Yarrowia lipolytica," Yeast, 14:1267-1283.

Nicaud (Oct. 5, 2012) "Yarrowia lipolytica," Yeast 29:409-418.

Nicaud et al. (2002) "Protein expression and secretion in the yeast *Yarrowia lipolytica*," FEMS Yeast Res. 2:371-379.

Papanikolaou et al. (2001) "Kinetic profile of the cellular lipid composition in an oleaginous Yarrowia lipolytica capable of producing a cocoa-butter substitute from industrial fats," Antonie van Leeuwenhoek. 80:215-224.

(56) References Cited

OTHER PUBLICATIONS

Papanikolaou et al. (2010) "Yarrowia lipolytica: A model microorganism used for the production of tailor-made lipids," Eur J Lipid Sci Technol. 112:639-654.
Papanikolaou et al. (Jun. 15, 2011) "Lipids of oleaginous yeasts. Part I: Biochemistry of single cell oil production," Eur J Lipid Sci Technol. 113:1031-1051.
Papanikolaou et al. (Jun. 15, 2011) "Lipids of oleaginous yeasts. Part II: Technology and potential applications," Eur J Lipid Sci Technol. 113:1052-1073.
Querol et al. (1992) "Molecular monitoring of wine fermentations conducted by active dry yeast strains," Appl Environ Microbiol. 58:2948-2953.
Rani et al. (Oct. 25, 2012) "A soluble diacylglycerol acyltransferase is involved in triacylglycerol biosynthesis in the oleaginous yeast *Rhodotorula glutinis*," Microbiology. 159:155-166.
Ratledge (2004) "Fatty acid biosynthesis in microorganisms being used for Single Cell Oil production," Biochimie. 86:807-815.
Smith et al. (2003) "Heterologous expression of a fatty acid hydroxylase gene in developing seeds of *Arabidopsis thaliana*," Planta. 217:507-516.

Wang et al. (1999) "Cloning, sequencing, and characterization of five genes coding for acyl-CoA oxidase isozymes in the yeast *Yarrowia lipolytica*," Cell Biochem Biophys. 31:165-174.
Wang et al. (1999) "Evaluation of acyl coenzyme A oxidase (Aox) isozyme function in they n-alkahe-assimilating yeast *Yarrowia lipolytica*," J Bacieriol. 181:5140-5148.
DePourcq et al. (2012) "Engineering the yeast *Yarrowia lipolytica* for the production of therapeutic proteins homogeneously glycosylated with $Man_8GlcNac_2$ and $Man_5GlcNac_2$," Microbial Cell Factories 11:53.
Guo et al. (2012) "Expression of POX2 gene and disruption of POX3 genes in the industrial Yarrowia lipolytica on the γ-decalactone production," Microbiological Research 167:246-252.
Kretzschmar et al. (2013) "Increased homologous integration frequency in Yarrowia lipolytica strains defective in non-homologous end-joining," Curr Genet 59:63-72.
Verbeke et al. (2013) "Efficient homologous recombination with short length flanking fragments in Ku70 deficient Yarrowia lipolytica strains," Biotechnol Lett 35:571-576.

\* cited by examiner

| Strains (host strains) | Plasmids, genotypes | References or sources |
|---|---|---|
| *E. coli* strains | | |
| DH5α | Φ80dlacZΔm15, recA1, endA1, gyrA96, thi-1, hsdR17 (r_k-, m_k+), supE44, relA1, deoR, Δ(lacZYA-argF)U169 | Promega |
| JME547 (DH5α) | pUB4-Cre1 (Cre ARS68 Hyg in) | Fickers et al, 2003 |
| JME791 (DH5α) | MU cassette, yiFAD2 PUT cassette | Present invention |
| JME803 (DH5α) | JMP62-pTEF-URA3ex | Nicaud et al., 2002 |
| JME804 (DH5α) | JMP62-pTEF-LEU2ex | Nicaud et al., 2002 |
| JME736 (DH5α) | MU cassette in JME735, yIDGA1 PUT cassette | Beopoulos et al., 2011 |
| JME738 (DH5α) | MU cassette in JME737, yILRO1 PUT cassette | Beopoulos et al., 2011 |
| JME996 (DH5α) | MU cassette in JME984, yIARE1 PUT cassette | Beopoulos et al., 2011 |
| JME1040 (DH5α) | MU cassette in JME984, yIDGA2 PLT cassette | Beopoulos et al., 2011 |
| JME1042 (DH5α) | MU cassette in JME984, yIDGA2 PUT cassette | Beopoulos et al., 2011 |
| JME1112 (DH5α) | JMP62-pTEF-DGA1-URA3ex | Beopoulos et al., 2011 |
| JME1114 (DH5α) | JMP62-pTEF-LRO1-URA3ex | Beopoulos et al., 2011 |
| JME1132 (DH5α) | JMP62-pTEF-DGA2-URA3ex | Beopoulos et al., 2011 |
| JME1215 (DH5α) | JMP62-pTEF-ARE1-URA3ex | Beopoulos et al., 2011 |
| JME1375 (DH5α) | JMP62-pTEF-RcFAH12-URA3ex | Present invention |
| JME1377 (DH5α) | JMP62-pTEF-RcDGAT2-LEU2ex | Present invention |
| JME1378 (DH5α) | JMP62-pTEF-CpFAH12-LEU2ex | Present invention |
| JME1403 (DH5α) | JMP62-pTEF-CpFAH12-URA3ex | Present invention |
| JME1406 (DH5α) | JMP62-pTEF-CpDGAT2-LEU2ex | Present invention |
| JME1619 (DH5α) | JMP62-pTef-ACL1-URA3ex | Present invention |
| JME1620 (DH5α) | JMP62-pTef-SLC1-URA3ex | Present invention |
| JME1622 (DH5α) | JMP62-pTef-SCT1-URA3ex | Present invention |
| JME1753 (DH5α) | JMP62-pTef-LPA1-URA3ex | Present invention |
| JME1754 (DH5α) | JMP62-pTef-LRO2-URA3ex | Present invention |
| JME1755 (DH5α) | JMP62-pTef-TGL5-URA3ex | Present invention |
| JME1756 (DH5α) | JMP62-pTef-EPT1-URA3ex | Present invention |
| JME1757 (DH5α) | JMP62-pTef-LCA3-URA3ex | Present invention |
| JME1849 (DH5α) | JMP62-pTef-ELOA-URA3ex | Present invention |
| JME1850 (DH5α) | JMP62-pTef-ELOB-URA3ex | Present invention |
| JME1851 (DH5α) | JMP62-pTef-MCR1-URA3ex | Present invention |
| JME1852 (DH5α) | JMP62-pTef-LCA1-URA3ex | Present invention |

FIG. 1

| Strain | Genotype | Reference |
|---|---|---|
| JME1853 (DH5a) | JMP62-pTef-LCA2-URA3ex | Present invention |
| JME1854 (DH5a) | JMP62-pTef-SAC2-URA3ex | Present invention |
| JME1855 (DH5a) | JMP62-pTef-ACL2-URA3ex | Beopoulos et al., 2009 |
| JME1857 (DH5a) | JMP62-pTef-CPT1-URA3ex | Present invention |
| JRE740 (DH5a) | PGEM-T-P-Ura3ex-T pHd1A | Papa/Racu et al., 2013 |
| JME1364 (DH5a) | pKS P-LEU2ex-T tgl4A | Dulermo et al., 2011 |

*Y. lipoytica* strains

| Strain | Genotype | Reference |
|---|---|---|
| Po1d | | |
| JMY1233 (MTLY97) | MATA ura3-302 leu2-270 xpr2-322 | Beopoulos et al., 2008 |
| JMY1356 | MATA ura3-302 leu2-270 xpr2-322 fad3Δ::URA3 | Present invention |
| JMY1366 | MATA ura3-302 leu2-270 xpr2-322 fad2Δ | Present invention |
| JMY1555 | MATA ura3-302 leu2-270 xpr2-322 pox1-6Δ tro1Δ::URA3 | Beopoulos et al., 2011 |
| JMY1557 | MATA ura3-302 leu2-270 xpr2-322 pox1-6Δ tro1Δ | Beopoulos et al., 2011 |
| JMY1609 | MATA ura3-302 leu2-270 xpr2-322 pox1-6Δ tro1Δ dga1Δ::URA3 | Beopoulos et al., 2011 |
| JMY1732 | MATA ura3-302 leu2-270 xpr2-322 pox1-6Δ tro1Δ dga1Δ | Beopoulos et al., 2011 |
| JMY1770 | MATA ura3-302 leu2-270 xpr2-322 fad2Δ pTEF-RcFAH12-URA3ex | Present invention |
| JMY1771 | MATA ura3-302 leu2-270 xpr2-322 pox1-6Δ fad2Δ::URA3 | Present invention |
| JMY1772 | MATA ura3-302 leu2-270 xpr2-322 pox1-6Δ fad2Δ | Present invention |
| JMY1773 | MATA ura3-302 leu2-270 xpr2-322 pox1-6Δ fad2Δ pTEF-RcFAH12-URA3ex | Present invention |
| JMY1774 | MATA ura3-302 leu2-270 xpr2-322 pox1-6Δ fad2Δ dga1Δ tro1Δ::URA3 | Present invention |
| JMY1775 | MATA ura3-302 leu2-270 xpr2-322 pox1-6Δ fad2Δ dga1Δ tro1Δ fad2Δ::URA3, dga2Δ::LEU2 | Present invention |
| JMY1877 | MATA ura3-302 leu2-270 xpr2-322 pox1-6Δ dga1Δ tro1Δ are1Δ dga2Δ | Beopoulos et al., 2011 |
| JMY1882 | MATA leu2-270 ura3-302 xpr2-322 pox1-6Δ dga1Δ tro1Δ are1Δ dga2Δ pTEF-LRO1-URA3ex | Beopoulos et al., 2011 |
| JMY1884 | MATA leu2-270 ura3-302 xpr2-322 pox1-6Δ dga1Δ tro1Δ are1Δ dga2Δ pTEF-DGA1-URA3ex | Beopoulos et al., 2011 |
| JMY1892 | MATA leu2-270 ura3-302 xpr2-322 pox1-6Δ dga1Δ tro1Δ are1Δ dga2Δ pTEF-DGA2-URA3ex | Beopoulos et al., 2011 |
| JMY1988 | MATA leu2-270 ura3-302 xpr2-322 pox1-6Δ dga1Δ tro1Δ are1Δ dga2Δ pTEF-ARE1-URA3ex | Beopoulos et al., 2011 |
| JMY2159 | MATA leu2-270 ura3-302 xpr2-322 pox1-6Δ dga1Δ tro1Δ dga2Δ fad2Δ | Present invention |
| JMY2232 | MATA ura3-302 leu2-270 xpr2-322 pox1-6Δ dga1Δ tro1Δ dga2Δ fad2Δ pTEF-RcDGAT2-LEU2ex | Present invention |
| JMY2235 | MATA ura3-302 leu2-270 xpr2-322 pox1-6Δ dga1Δ tro1Δ dga2Δ fad2Δ pTEF-RcDGAT2-LEU2ex pTEF-RcFAH12-URA3ex | Present invention |
| JMY2324 | MATA ura3-302 leu2-270 xpr2-322 pox1-6Δ dga1Δ tro1Δ dga2Δ fad2Δ pTEF-CpFAH12-URA3ex | Present invention |
| JMY2329 | MATA ura3-302 leu2-270 xpr2-322 pox1-6Δ dga1Δ tro1Δ dga2Δ fad2Δ pTEF-CpFAH12-URA3ex, pTEF-RcDGAT2-LEU2ex | Present invention |
| JMY2331 | MATA ura3-302 leu2-270 xpr2-322 pox1-6Δ dga1Δ tro1Δ dga2Δ fad2Δ pTEF-CpFAH12-URA3ex pTEF-RcFAH12-LEU2ex | Present invention |
| JMY2345 | MATA ura3-302 leu2-270 xpr2-322 pox1-6Δ dga1Δ tro1Δ dga2Δ fad2Δ pTEF-CpFAH12-URA3ex, pTEF-CpFAH12-LEU2ex | Present invention |
| JMY2393 | MATA ura3-302 leu2-270 xpr2-322 pox1-6Δ dga1Δ tro1Δ dga2Δ fad2Δ pTEF-CpFAH12-URA3ex, pTEF-CpDGAT2-LEU2ex | Present invention |

FIG. 1 (continued)

| Strain | Genotype | Source |
|---|---|---|
| JMY2511 | MATA ura3-302 leu2-270 xpr2-322 pox1-6Δ dga1Δ lro1Δ dga2Δ fad2Δ pTEF-CpFAH12, pTEF-CpFAH12-URA3ex | Present invention |
| JMY2517 | MATA ura3-302 leu2-270 xpr2-322 pox1-6Δ dga1Δ lro1Δ dga2Δ fad2Δ pTEF-CpFAH12-URA3ex, pTEF-CpDGAT2 | Present invention |
| JMY2527 | MATA ura3-302 leu2-270 xpr2-322 pox1-6Δ dga1Δ lro1Δ dga2Δ fad2Δ pTEF-CpFAH12x2 | Present invention |
| JMY2556 | MATA ura3-302 leu2-270 xpr2-322 pox1-6Δ dga1Δ lro1Δ dga2Δ fad2Δ pTEF-CpFAH12x2 pTEF-LRO1-URA3ex | Present invention |
| JMY2853 | MATA ura3-302 leu2-270 xpr2-322 pox1-6Δ dga1Δ lro1Δ dga2Δ fad2Δ pTEF-CpFAH12x2 pTEF-LRO1 | Present invention |
| JMY3024 | MATA ura3-302 leu2-270 xpr2-322 pox1-6Δ dga1Δ lro1Δ dga2Δ fad2Δ pTEF-CpFAH12x2 pTEF-LRO1 pTEF-ACL1-URA3ex | Present invention |
| JMY3026 | MATA ura3-302 leu2-270 xpr2-322 pox1-6Δ dga1Δ lro1Δ dga2Δ fad2Δ pTEF-CpFAH12x2 pTEF-LRO1 pTEF-SLC1-URA3ex | Present invention |
| JMY3030 | MATA ura3-302 leu2-270 xpr2-322 pox1-6Δ dga1Δ lro1Δ dga2Δ fad2Δ pTEF-CpFAH12x2 pTEF-LRO1 pTEF-CpFAH12-URA3ex pTef-LRO1-LEU2ex | Present invention |
| JMY3285 | MATA ura3-302 leu2-270 xpr2-322 pox1-6Δ dga1Δ lro1Δ dga2Δ fad2Δ pTEF-CpFAH12x2 pTEF-LRO1 pTEF-MCR1-URA3ex | Present invention |
| JMY3286 | MATA ura3-302 leu2-270 xpr2-322 pox1-6Δ dga1Δ lro1Δ dga2Δ fad2Δ pTEF-CpFAH12x2 pTEF-LRO1 pTEF-LCA1-URA3ex | Present invention |
| JMY3288 | MATA ura3-302 leu2-270 xpr2-322 pox1-6Δ dga1Δ lro1Δ dga2Δ fad2Δ pTEF-CpFAH12x2 pTEF-LRO1 phd1::URA3ex | Present invention |
| JMY3289 | MATA ura3-302 leu2-270 xpr2-322 pox1-6Δ dga1Δ lro1Δ dga2Δ fad2Δ pTEF-CpFAH12x2 pTEF-LRO1 pTEF-LCA3-URA3ex | Present invention |
| JMY3290 | MATA ura3-302 leu2-270 xpr2-322 pox1-6Δ dga1Δ lro1Δ dga2Δ fad2Δ pTEF-CpFAH12x2 pTEF-LRO1 pTEF-ELOA-URA3ex | Present invention |
| JMY3291 | MATA ura3-302 leu2-270 xpr2-322 pox1-6Δ dga1Δ lro1Δ dga2Δ fad2Δ pTEF-CpFAH12x2 pTEF-LRO1 pTEF-CPT1-URA3ex | Present invention |
| JMY3293 | MATA ura3-302 leu2-270 xpr2-322 pox1-6Δ dga1Δ lro1Δ dga2Δ fad2Δ pTEF-CpFAH12x2 pTEF-LRO1 pTEF-LCA2-URA3ex | Present invention |
| JMY3294 | MATA ura3-302 leu2-270 xpr2-322 pox1-6Δ dga1Δ lro1Δ dga2Δ fad2Δ pTEF-CpFAH12x2 pTEF-LRO1 pTEF-LPA1-URA3ex | Present invention |
| JMY3295 | MATA ura3-302 leu2-270 xpr2-322 pox1-6Δ dga1Δ lro1Δ dga2Δ fad2Δ pTEF-CpFAH12x2 pTEF-LRO1 pTEF-EPT1-URA3ex | Present invention |
| JMY3296 | MATA ura3-302 leu2-270 xpr2-322 pox1-6Δ dga1Δ lro1Δ dga2Δ fad2Δ pTEF-CpFAH12x2 pTEF-LRO1 pTEF-SAC1-URA3ex | Present invention |
| JMY3297 | MATA ura3-302 leu2-270 xpr2-322 pox1-6Δ dga1Δ lro1Δ dga2Δ fad2Δ pTEF-CpFAH12x2 pTEF-LRO1 pTEF-LRO2-URA3ex | Present invention |
| JMY3298 | MATA ura3-302 leu2-270 xpr2-322 pox1-6Δ dga1Δ lro1Δ dga2Δ fad2Δ pTEF-CpFAH12x2 pTEF-LRO1 pTEF-ELOB-URA3ex | Present invention |
| JMY3299 | MATA ura3-302 leu2-270 xpr2-322 pox1-6Δ dga1Δ lro1Δ dga2Δ fad2Δ pTEF-CpFAH12x2 pTEF-LRO1 pTEF-TGL5-URA3ex | Present invention |
| JMY3300 | MATA ura3-302 leu2-270 xpr2-322 pox1-6Δ dga1Δ lro1Δ dga2Δ fad2Δ pTEF-CpFAH12x2 pTEF-LRO1 pTEF-ACL2-URA3ex | Present invention |
| JMY3431 | MATA ura3-302 leu2-270 xpr2-322 pox1-6Δ dga1Δ lro1Δ dga2Δ fad2Δ pTEF-CpFAH12x3 pTEF-LRO1x2 | Present invention |
| JMY4441 | MATA ura3-302 leu2-270 xpr2-322 pox1-6Δ dga1Δ lro1Δ dga2Δ fad2Δ pTEF-CpFAH12x3 pTEF-LRO1x2 pTEF-SLC1-URA3ex | Present invention |
| JMY4442 | MATA ura3-302 leu2-270 xpr2-322 pox1-6Δ dga1Δ lro1Δ dga2Δ fad2Δ pTEF-CpFAH12x3 pTEF-LRO1x2 pTEF-MCR1-URA3ex | Present invention |
| JMY4444 | MATA ura3-302 leu2-270 xpr2-322 pox1-6Δ dga1Δ lro1Δ dga2Δ fad2Δ pTEF-CpFAH12x3 pTEF-LRO1x2 pTEF-CPT1-URA3ex | Present invention |
| JMY4447 | MATA ura3-302 leu2-270 xpr2-322 pox1-6Δ dga1Δ lro1Δ dga2Δ fad2Δ pTEF-CpFAH12x3 pTEF-LRO1x2 pTEF-LCA1-URA3ex | Present invention |

FIG. 1 (continued)

| Primers | Sequences (5'-3') | Restriction site introduced | SEQ ID NO.: |
|---|---|---|---|
| **Oleate dehydrogenase of *Y. lipolytica*** | | | |
| yiΔ12-ver1 | GTATCAAGTTGCCCATTGTGTTGTATGTTCC | | 1 |
| yiΔ12-P1 | GTACCCGTACAAGTAGTTAAGCATAG | | 2 |
| yiΔ12-P2 | GCATTACCCTGTTATCCCTAGCGGTGTTGGTCTGCGTGGTC | IsceI | 3 |
| yiΔ12-T1 | GCTAGGGATAACAGGGTAATGCGTTGCTGAGGACGCTCCCC | IsceI | 4 |
| yiΔ12-T2 | CCATGAACGCAGACACGCAG | | 5 |
| yiΔ12-ver2 | GGAAACTACAACGGTTGTCAGCGTAATG | | 6 |
| **Oleate hydroxylase of *R. communis*** | | | |
| RcFAH12f | GCCGAATGTCTACCGTGATCACCTCTAACTGTCTACCGTG | | 7 |
| RcFAH12r | CTCGACGAACAGGCACTCCTTGGCCTCTCGC | | 8 |
| **Acyl-CoA:diacylglycerol acyl transferase type II of *R. communis*** | | | |
| RcDAGATf | GAACTCTCGAGAGCTGTACCCCACCAACATCTTCCACG | | 9 |
| RcDAGATr | GTCGGCGTAGCCCACTCGGGCCTTGTGTC | | 10 |
| **Oleate hydroxylase of *C. purpurea*** | | | |
| CpFAH12f | CATGTCTGAGAACGCCGTGCTGCGACACAAGGC | | 11 |
| CpFAH12r | GTCAGATCGGTAGTGCTTGCCCATGATGGGCTTGATAGC | | 12 |
| **Acyl-CoA:diacylglycerol acyl transferase type II of *C. purpurea*** | | | |
| CpDGAT2f | GACTCACGAGCCCCTCGAGCTGAACGGCTCTGC | | 13 |
| CpDGAT2r | GAGAACTGTTCCTTGTAGGCGGCGTACAGTCGCTCG | | 14 |
| **Phospholipid:diacylglycerol acyl transferase of *Y. lipolytica*** | | | |
| LRO1_F | CTCCGCCGACTTCTTTATG | | 15 |
| LRO1_R | GAAGTATCCGTCTCGGTG | | 16 |
| **β-isopropylmalate dehydrogenase of *Y. lipolytica*** | | | |
| Leu2sens | CGCTGTTGAGGCTGCCGTCAAGGAGTCCG | | 17 |
| Leu2rev | CGGACTCCTTGACGGCAGCCTCAACAGCG | | 18 |
| **Orotidine-5'-phosphate decarboxylase of *Y. lipolytica*** | | | |
| Ura3sens | CGGCCAGCATGAGCAGACCTCTGGCCAG | | 19 |
| Ura3rev | CTGGCCAGAGGTCTGCTCATGCTGGCCG | | 20 |

FIG. 3

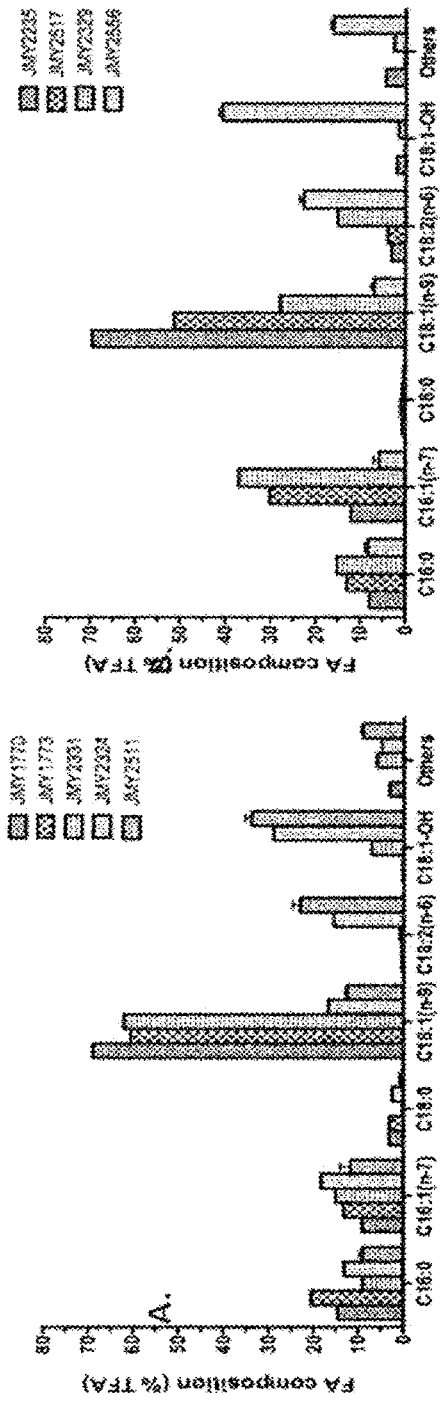

Figure 4A

*Strains expressing hydroxylase in different genetic backgrounds*

| strain | genotype |
|---|---|
| JMY1770 | fad2ΔpTEF-RcFAH12 |
| JMY1773 | pox1-6Δfad2ΔpTEF-RcFAH12 |
| JMY2331 | pox1-6Δfad2Δdga1Δdga2Δlro1pTEF-RcFAH12 |
| JMY2324 | pox1-6Δfad2Δdga1Δdga2Δlro1pTEF-CpFAH12 |
| JMY2511 | pox1-6Δfad2Δdga1Δdga2Δlro1pTEF-CpFAH12x2 |

Figure 4B

*Strains co-expressing hydroxylase and desaturase in different genetic backgrounds*

| strain | genotype |
|---|---|
| JMY2235 | pox1-6Δfad2Δdga1Δdga2Δlro1pTEF-RcFAH12-ReDGAT2 |
| JMY2517 | pox1-6Δfad2Δdga1Δdga2Δlro1pTEF-CpFAH12-CpDGAT2 |
| JMY2329 | pox1-6Δfad2Δdga1Δdga2Δlro1pTEF-CpFAH12-RcDGAT2 |
| JMY2556 | pox1-6Δfad2Δdga1Δdga2Δlro1pTEF-CpFAH12x2-YlLRO1 |

| Primers | Sequences (5'-3') | Restriction sites | SEQ ID NO: |
|---|---|---|---|
| Subunit A of ATP citrate lyase | | | |
| ACL1-S | CGCGGATCCCACAATGTCTGCCAACGAGAACATCTCCCGATTCGAC | BamHI | 25 |
| ACL1-A | CACCCTAGGTCTATGATCGAGTCTTGGCCTTGGAAACGTC | AvrII | 26 |
| Subunit B of ATP citrate lyase | | | |
| ACL2-A | CACGGATCCCACAATGTCAGCGAAATCCATTCACGAGGCCGAC | BamHI | 27 |
| ACL2-B | ATGCCTAGGTTAAACTCCGAGAGGAGTGGAAGCCTCAGTAGAAG | AvrII | 28 |
| ACL2-C | GAGAGGGCGACTGGATTCTCTTCTACCAC | Deletion of the BamHI site | 29 |
| ACL2-D | GTGGTAGAAGAGAATCCAGTCGCCCTCTC | Deletion of the BamHI site | 30 |
| ACL2-E | CTTCACCCAGGTTGGCTCCACCTTCAAGGGC | Deletion of the BamHI site | 31 |
| ACL2-F | GCCCTTGAAGGTGGAGCCAACCTGGGTGAAG | Deletion of the BamHI site | 32 |
| Elongase B | | | |
| ELO2for | CGGGATCCTCGCCAGTTGTACTCTCGTTG | BamHI | 33 |
| ELO2rev | CCTAGGTTATGCTCGTCGAGATCGGGTAGTGG | AvrII | 34 |
| Elongase A | | | |
| ELO1for | GCAACGGATCCACATCACAAAATGCTCTCGTCAATCTCGCCCGA | BamHI | 35 |
| ELO1rev | CAGACACCCTAGGGTCTGAATGACTTGGGAGCAGGAGAG | AvrII | 36 |
| Diacylglycerol:choline-O phosphotransferase 1 | | | |
| CPT1for | CGTGGATCCCACAATGGGTAAAAGCCCCTCTATGATTGGGAC | BamHI | 37 |
| CPT1rev | CCCCTAGGCTAGTTGGTCTTGTTGTCCACGGGTC | AvrII | 38 |
| Cytochrome-b$_5$ reductase | | | |
| MCR1for | CGTGGATCCCACAATGCTTGTGGTTGGTGGAAACAGAGAAAACCGG | BamHI | 39 |
| MCR1rev | CCCCTAGGTTAGAACTTGAAGACCTGGTCCTTGTTGAAACC | AvrII | 40 |
| Cytochrome-b$_5$ reductase | | | |
| CBR1for | CGTGGATCCCACAATGCGCTCCTCTTCTTCACGACAACC | BamHI | 41 |
| CBR1rev | CCCCTAGGTTAAAAGGCAAAGACCTGATCCTCAAGTTTGCTG | AvrII | 42 |
| Acyl-CoA:lysophosphatidylcholine acyl transferase 1 | | | |
| F19514for | CGTGGATCCCACAATGGCCTTTCCATGGGCAGATAAGTGG | BamHI | 43 |
| F19514rev | CCCCTAGGTTACTTGGTCTTGATGGTGTCCTTCTTCACC | AvrII | 44 |
| Acyl-CoA:lysophosphatidylcholine acyl transferase 2 | | | |
| C20625for | CGTGGATCCCACAATGCTTATCAAGGAATCCTACCACGACGTCAAAACC | BamHI | 45 |
| C20625rev | CCCCTAGGCTAACAAACGTCCTCGACCTTCTCCTCG | AvrII | 46 |
| Phospholipase A$_2$ | | | |
| PAPfor | CGTGGATCCCACAATGAAATACGCAGAGGACCACAACGGCTAC | BamHI | 47 |
| PAPrev | CCCCTAGGCTAATCCAGCTTGTTGACCCGGTCGCT | AvrII | 48 |

FIG. 6

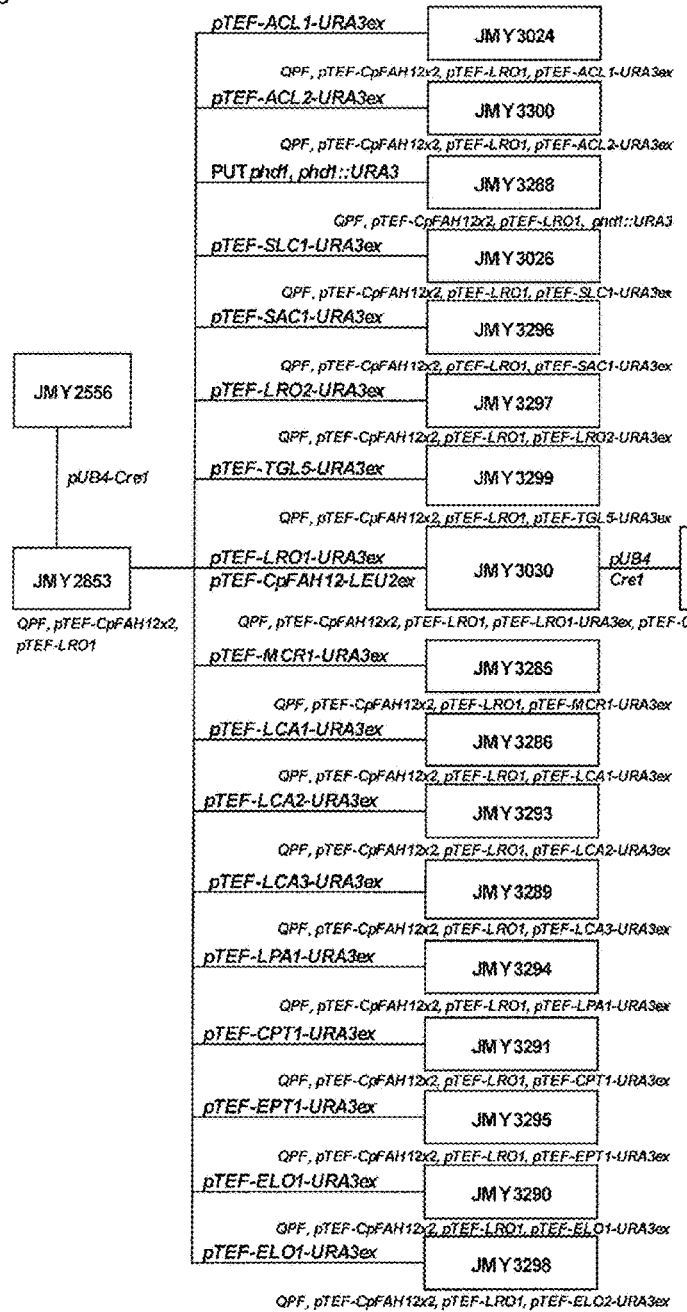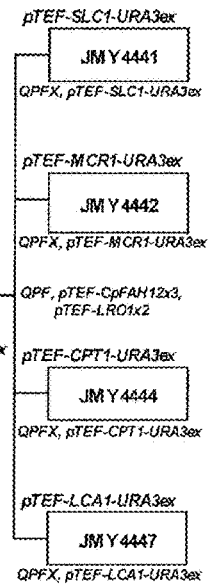
Figure 8A
Figure 8B

Figure 9A

| Y. lipolytica strain | Modification in JMY2853 | Effect on RA production (% relative to JMY2556) |
|---|---|---|
| JMY3030 | + LRO1 + CpFAH12 | + 330 |
| JMY3024 | + ACL1 (YALI0E34793g) | + 45 |
| JMY3300 | + ACL2 (YALI0D24431g) | + 86 |
| JMY3288 | - phd1Δ (YALI0F02497g) | + 111 |
| JMY3026 | + SLC1 (YALI0E18964g) | + 95 |
| JMY3296 | + SAC1 (YALI0D05995g) | + 58 |
| JMY3297 | + LRO2 (YALI0E08206g) | + 25 |
| JMY3299 | + TGL5 (YALI0D16379g) | + 56 |
| JMY3285 | + MCR1 (YALI0D11330g) | + 175 |
| JMY3286 | + LCA1 (YALI0F19514g) | + 51 |
| JMY3293 | + LCA2 (YALI0C20625g) | + 4 |
| JMY3289 | + LCA3 (YALI0C14036G) | + 34 |
| JMY3294 | + LPA1 (YALI0F1001g) | + 85 |
| JMY3291 | + CPT1 (YALI0E26565g) | + 92 |
| JMY3295 | + EPT1 (YALI0C10989g) | + 27 |
| JMY3290 | + ELO1 (YALI0F06754g) | + 38 |
| JMY3298 | + ELO2 (YALI0B20196g) | + 42 |

Figure 9B

| Y. lipolytica strain | Modification in JMY3431 | Effect on RA production (% relative to JMY3030) |
|---|---|---|
| JMY4441 | + SLC1 (YALI0E18964g) | - 3 |
| JMY4442 | + MCR1 (YALI0D11330g) | + 50 |
| JMY4444 | + CPT1 (YALI0E26565g) | - 36 |
| JMY4447 | + LCA1 (YALI0F19514g) | + 21 |

SEQUENCE LISTING

```
<160> NUMBER OF SEQ ID NOS: 51

<210> SEQ ID NO 1
<211> LENGTH: 31
<212> TYPE: DNA
<213> ORGANISM: Artificial Sequence
<220> FEATURE:
<223> OTHER INFORMATION: Primer

<400> SEQUENCE: 1
gtatcaagtt gcccattgtg ttgtatgttc c                           31

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
gtacccgtac aagtagttaa gcatag                                 26

<210> SEQ ID NO 3
<211> LENGTH: 41
<212> TYPE: DNA
<213> ORGANISM: Artificial Sequence
<220> FEATURE:
<223> OTHER INFORMATION: Primer

<400> SEQUENCE: 3
gcattaccct gttatcccta gcggtgttgg tctgcgtggt c                41

<210> SEQ ID NO 4
<211> LENGTH: 41
<212> TYPE: DNA
<213> ORGANISM: Artificial Sequence
<220> FEATURE:
<223> OTHER INFORMATION: Primer

<400> SEQUENCE: 4
gctagggata acagggtaat gcgttgctga ggacgctccc c                41

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ccatgaacgc agacacgcag                                        20

<210> SEQ ID NO 6
<211> LENGTH: 28
<212> TYPE: DNA
<213> ORGANISM: Artificial Sequence
<220> FEATURE:
<223> OTHER INFORMATION: Primer
```

```
<400> SEQUENCE: 6
ggaaactaca acggttgtca gcgtaatg                                        28

<210> SEQ ID NO 7
<211> LENGTH: 40
<212> TYPE: DNA
<213> ORGANISM: Artificial Sequence
<220> FEATURE:
<223> OTHER INFORMATION: Primer

<400> SEQUENCE: 7
gccgaatgtc taccgtgatc acctctaact gtctaccgtg                           40

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
ctcgacgaac aggcactcct tggcctctcg c                                    31

<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9
gaactctcga gagctgtacc ccaccaacat cttccacg                             38

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
gtcggcgtag cccactcggg ccttgtgtc                                       29

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
catgtctgag aacgccgtgc tgcgacacaa ggc                                  33

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
gtcagatcgg tagtgcttgc ccatgatggg cttgatagc                            39
```

```
<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
gactcacgag cccctcgagc tgaacggctc tgc                        33

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
gagaactgtt ccttgtaggc ggcgtacagt cgctcg                     36

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
ctccgccgac ttctttatg                                        19

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
gaagtatccg tctcggtg                                         18

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
cgctgttgag gctgccgtca aggagtccg                             29

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
cggactcctt gacggcagcc tcaacagcg                             29

<210> SEQ ID NO 19
<211> LENGTH: 28
<212> TYPE: DNA
<213> ORGANISM: Artificial Sequence
<220> FEATURE:
<223> OTHER INFORMATION: Primer
```

<400> SEQUENCE: 19
cggccagcat gagcagacct ctggccag                                              28

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
ctggccagag gtctgctcat gctggccg                                              28

<210> SEQ ID NO 21
<211> LENGTH: 1192
<212> TYPE: DNA
<213> ORGANISM: Artificial Sequence
<220> FEATURE:
<223> OTHER INFORMATION: Synthetic RcFAH12

<400> SEQUENCE: 21
gagctcggat cccacaatgg gcggaggcgg ccgaatgtct accgtgatca cctctaacaa    60
ctccgagaag aagggcggat cttctcacct gaagcgagcc cccacacca agccccttt    120
caccctgggc gacctcaagc gagccatccc ccccactgc ttcgaacgat ctttcgtgcg    180
atccttctct tacgtggcct acgacgtgtg cctgtctttc ctgttctact cgatcgctac    240
caacttcttc ccctacatct cttcgcccct gtcctacgtg gcctggctgg tgtactggct    300
gttccagggc tgcatcctga ccggcctgtg ggtcatcggc cacagtgtg gccaccacgc    360
cttctctgag taccagctgg ccgacgacat cgtgggcctg atcgtgcact ctgccctgct    420
ggtgccctac ttctcttgga gtactctca ccgacgacac cactctaaca tcggatctct    480
cgagcgagac gaggtgttcg tgcccaagtc taagtctaag atctcctggt actccaagta    540
cctgaacaac cccccctggc cgagtgctga cctggctgct accctgctgc tgggctggcc    600
cctgtacctg gccttcaacg tgtccggccg accctacgac cgattcgcct gccactacga    660
cccctacggc cccatcttct ctgagcgaga gcgactgcag atctacattg ccgacctggg    720
catcttcgcc accaccttcg tgctgtacca ggccaccatg gccaagggcc tggcctgggt    780
catgcgaatc tacggcgtgc ccctgctgat cgtgaactgc ttcctggtca tgatcaccta    840
cctgcagcac acccacccg ccatcccccg atacggatct tctgagtggg actggctgcg    900
aggcgccatg gtcaccgtgg accgagacta cggcgtcctg aacaaggtgt ccacaaacat    960
tgctgacacc cacgtggccc accacctgtt cgccaccgtg ccccactacc acgccatgga    1020
ggccaccaag gctatcaagc ccatcatggg cgagtactac cgatacgacg cacacccctt    1080
ctacaaggcc ctgtggcgag aggccaagga gtgcctgttc gtcgagcccg acgagggtgc    1140
tcccacccag ggcgtgttct ggtaccgaaa caagtattaa cctaggggta cc              1192

<210> SEQ ID NO 22
<211> LENGTH: 1462
<212> TYPE: DNA
<213> ORGANISM: Artificial Sequence
<220> FEATURE:
<223> OTHER INFORMATION: Synthetic CpFAH12

<400> SEQUENCE: 22
gagctcggat cccacaatgg cctctgccac cccgccatg tctgagaacg ccgtgctgcg    60
acacaaggcc gcctctacca ccggaatcga ctacgagtcc tctgccgccg tgtctcccgc    120

```
cgagtctccc cgaacctctg cctcttctac ctcgctgtcc tctctgtcct ccctggacgc      180
caacgagaag aaggacgagt acgccggcct gctggacacc tacggcaacg ccttcacccc      240
ccctgacttc tctatcaagg acatccgagc cgccatcccc aagcactgct acgagcgatc      300
taccatcaag tcttacgcct acgtgctgcg agatctgctg tgcctgtcta ccaccttcta      360
cctgttccac aacttcgtga cccccgagaa catcccctct aacccctgc gattcgtgct       420 gtggtctatc tacaccgtgc tgcagggcct gttcgccacc ggcctgtggg tgatcggcca      480
cgagtgcggc cactgcgcct ctctccctc tcccttcatc tctgacctga ccggctgggt       540
gatccactct gccctgctgg tgccctactt ctcttggaag ttctctcact ctgcccacca      600
caagggcatc ggcaacatgg agcgagacat ggtgtttctg ccccgaaccc gagagcagca     660
ggccacccga ctgggccgag ccgtcgagga gctgggcgac ctgtgcgagg agactcccat      720
ctacaccgcc ctgcacctgg tgggcaagca gctgatcggc tggcccctctt acctgatgac    780 caacgctacc ggccacaact tccacgagcg acagcgagag ggccgaggca gggcaagaa      840 gaacggcttc ggcggaggcg tgaaccactt cgacccccga tctcccatct tcgaggcccg     900
acaggccaag tacatcgtgc tgtctgacat cggcctgggc ctggccattg ccgccctggt    960
gtacctgggc aaccgattcg gctgggccaa catggccgtg tggtactttc tgccctacct     1020
gtgggtgaac cactggctgg tggctatcac cttcctgcag cacaccgacc ccaccctgcc     1080
ccactacaac cgagaggagt ggaacttcgt gcgaggcgga gcctgcacca tcgaccgaga    1140
tctgggcttc atcggccgac acctgttcca cggaatcgcc gacacccacg tggtgcatca     1200
ctacgtgtct cgaatcccct tctacaacgc cgacagggcc tctgaggcta tcaagcccat     1260
catgggcaag cactaccgat ctgacaccgc tcacggcccc gtgggctttc tgcacgccct      1320
gtggaagacc gccgatggt gccagtgggt cgagccctct gccgacgctc agggcgctgg       1380
caagggcatc ctgttctacc gaaaccgaaa caagctgggc accaagccca tctctatgaa     1440
gacccagtaa cctaggggta cc                                                 1462

<210> SEQ ID NO 23
<211> LENGTH: 1051
<212> TYPE: DNA
<213> ORGANISM: Artificial Sequence
<220> FEATURE:
<223> OTHER INFORMATION: Synthetic RcDGAT2

<400> SEQUENCE: 23
gagctcggat cccacaatgg gcgaggaagc caaccataac aacaacaaca acaacatcaa       60
ctccaacgac gagaagaacg aggaaaagtc taactacacc gtggtgaact ctcgagagct      120
gtaccccacc aacatcttcc acgccctgct ggccctgtct atctggatcg gctctatcca     180
cttcaacctg tttctgctgt ttatctctta cctgttcctg tctttcccca ccttcctgct      240
gatcgtgggc ttcttcgtgg tgctgatgtt catccccatc gacgagcact ctaagctggg      300
ccgacgactg tgccgatacg tgtgccgaca cgcctgctct cacttccccg tgaccctgca      360
cgtcgaggac atgaacgcct tccactctga ccagcctac gtgttcggct acgagcccca      420
ctctgtgttc ccctgggcg tgtctgtgct gtctgaccac ttcgccgtgc tgccctgcc       480 caagatgaag gtgctggcct taacgccgt gttccgaacc ccgtgctgc acacatctg       540 gacctggtgc ggcctgacct ctgccaccaa gaagaacttc accgctctgc tcgctctgg      600 ctactcttgc atcgtgattc ccggcggagt gcaagaaact ttctacatga gcacggctc      660 tgagatcgcc ttcctgaagg cccgacgagg cttcgtgcga gtggccatgg aaatgggtaa     720
```

```
gcccctggtg cccgtgttct gcttcggcca gtctaacgtg tacaagtggt ggaagcccga    780
cggcgagctg ttcatgaaga tcgcccgagc catcaagttc tctcccatcg tgttctgggg    840
cgtgctgggc tctcatctgc ctctgcagcg acccatgcac gtggtggtgg gcaagcccat    900
cgaggtgaag cagaaccccc agcccaccgt cgaggaagtg tctgaggtcc agggccagtt    960
cgtggccgcc ctgaaggacc tgttcgagcg acacaaggcc cgagtgggct acgccgacct   1020
gaccctcgag atcctgtaac ctaggggtac c                                   1051
```

<210> SEQ ID NO 24
<211> LENGTH: 1342
<212> TYPE: DNA
<213> ORGANISM: Artificial Sequence
<220> FEATURE:
<223> OTHER INFORMATION: Synthetic CpDGAT2

<400> SEQUENCE: 24

```
gagctcggat cccacaatgg ccgccgtgca ggttgctcga cccgtgcctc ctcaccacca     60
cgacggtgct ggccgagagc acaagggtga gcgagcccac tctcccgagc gaggcgaaaa    120
gaccgtgcac aacggctacg gcctggccga gactcacgag cccctcgagc tgaacggctc    180
tgctgtgcag gacggcaagc acgactctga cgagactatc accaacggcg actactctcc    240
ctaccccgag ctggactgcg caaggaacg agccgcccac gagaaggaag cctggactgc    300
tggcggcgtg cgattcgctc ccctgcgagt gcccttcaag cgacgaatgc agaccgccgc    360
tgtgctgttc cactgcatgt ctattatcct gatctcttct tgcttctggt tctctctggc    420
caaccccatc acctggccca tcctggtgcc ttacctggtg cacctgtctc tgtctaacgc    480
ctctaccgac ggcaagctgt cttaccgatc tgagtggctg cgatctctgc ccctgtggcg    540
actgttcgcc ggctacttcc ccgccaagct gcacaagacc ttcgacctgc cccccaaccg    600
aaagtacatc ttcggctacc accccacgg catcatctct cacggcgcct ggtgcgcctt    660
cgccaccaac gctctgggct tcgtcgagaa gttccccggc atcaccaact ccctgctgac    720
cctggactct aacttccgag tgcctttcta ccgagactgg attctggcca tgggcatccg    780
atctgtgtct cgagagtcta tccgaaacat cctgtctaag gcggaccccg actctaacgg    840
ccagggacga ccgtgacca tcgtgattgg cggtgctcga gagtccctcg aggcccagcc    900
tggaaccctg cgactgatcc tgcagggccg aaagggcttc atcaaggtgg ccctgcgagc    960
cggcgctgac ctggtgcccg tgatcggctt cggcgagaac gacctgtacg accagctgtc   1020
tcccaagacc cacccctgg tgcacaagat ccagatggtg ttcctgaagg tgttcaagtt   1080
caccatcccc gccctgcacg gccgaggcct gctgaactac gacgtgggcc tgctgcccta   1140
ccgacgagcc gtcaacattg tggtgggccg acccatccag atcgacgaga cttacgcga   1200 gcagccccc caggaagtga tcgaccgata ccacgagctg tacgtgcagg aagtcgagcg   1260
actgtacgcc gcctacaagg aacagttctc taacggcaag aagaccccg agctgcagat   1320 cctgtcttaa cctaggggta cc                                           1342
```

<210> SEQ ID NO 25
<211> LENGTH: 46
<212> TYPE: DNA
<213> ORGANISM: Artificial Sequence
<220> FEATURE:
<223> OTHER INFORMATION: Primer

<400> SEQUENCE: 25

```
cgcggatccc acaatgtctg ccaacgagaa catctcccga ttcgac                    46
```

<210> SEQ ID NO 26
<211> LENGTH: 40
<212> TYPE: DNA
<213> ORGANISM: Artificial Sequence
<220> FEATURE:
<223> OTHER INFORMATION: Primer

<400> SEQUENCE: 26
caccctaggt ctatgatcga gtcttggcct tggaaacgtc    40

<210> SEQ ID NO 27
<211> LENGTH: 43
<212> TYPE: DNA
<213> ORGANISM: Artificial Sequence
<220> FEATURE:
<223> OTHER INFORMATION: Primer

<400> SEQUENCE: 27
cacggatccc acaatgtcag cgaaatccat tcacgaggcc gac    43

<210> SEQ ID NO 28
<211> LENGTH: 44
<212> TYPE: DNA
<213> ORGANISM: Artificial Sequence
<220> FEATURE:
<223> OTHER INFORMATION: Primer

<400> SEQUENCE: 28
atgcctaggt taaactccga gaggagtgga agcctcagta gaag    44

<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29
gagagggcga ctggattctc ttctaccac    29

<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30
gtggtagaag agaatccagt cgccctctc    29

<210> SEQ ID NO 31
<211> LENGTH: 31
<212> TYPE: DNA
<213> ORGANISM: Artificial Sequence
<220> FEATURE:
<223> OTHER INFORMATION: Primer

<400> SEQUENCE: 31
cttcacccag gttggctcca ccttcaaggg c    31

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32
gcccttgaag gtggagccaa cctgggtgaa g     31

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
cgggatcctc gccagttgta ctctcgttg     29

<210> SEQ ID NO 34
<211> LENGTH: 32
<212> TYPE: DNA
<213> ORGANISM: Artificial Sequence
<220> FEATURE:
<223> OTHER INFORMATION: Primer

<400> SEQUENCE: 34
cctaggttat gctcgtcgag atcgggtagt gg     32

<210> SEQ ID NO 35
<211> LENGTH: 44
<212> TYPE: DNA
<213> ORGANISM: Artificial Sequence
<220> FEATURE:
<223> OTHER INFORMATION: Primer

<400> SEQUENCE: 35
gcaacggatc cacatcacaa aatgctctcg tcaatctcgc ccga     44

<210> SEQ ID NO 36
<211> LENGTH: 39
<212> TYPE: DNA
<213> ORGANISM: Artificial Sequence
<220> FEATURE:
<223> OTHER INFORMATION: Primer

<400> SEQUENCE: 36
cagacaccct agggtctgaa tgacttggga gcaggagag     39

<210> SEQ ID NO 37
<211> LENGTH: 42
<212> TYPE: DNA
<213> ORGANISM: Artificial Sequence
<220> FEATURE:
<223> OTHER INFORMATION: Artificial

<400> SEQUENCE: 37
cgtggatccc acaatgggta aaagcccctc tatgattggg ac     42

<210> SEQ ID NO 38
<211> LENGTH: 34
<212> TYPE: DNA
<213> ORGANISM: Artificial Sequence
<220> FEATURE:
<223> OTHER INFORMATION: Artificial

<400> SEQUENCE: 38
cccctaggct agttggtctt gttgtccacg ggtc     34

<210> SEQ ID NO 39
<211> LENGTH: 46
<212> TYPE: DNA
<213> ORGANISM: Artificial Sequence
<220> FEATURE:
<223> OTHER INFORMATION: Primer

<400> SEQUENCE: 39
cgtggatccc acaatgcttg tggttggtgg aaacagagaa aaccgg            46

<210> SEQ ID NO 40
<211> LENGTH: 41
<212> TYPE: DNA
<213> ORGANISM: Artificial Sequence
<220> FEATURE:
<223> OTHER INFORMATION: Primer

<400> SEQUENCE: 40
cccctaggtt agaacttgaa gacctggtcc ttgttgaaac c                  41

<210> SEQ ID NO 41
<211> LENGTH: 39
<212> TYPE: DNA
<213> ORGANISM: Artificial Sequence
<220> FEATURE:
<223> OTHER INFORMATION: Primer

<400> SEQUENCE: 41
cgtggatccc acaatgcgct cctcttcttc acgacaacc                     39

<210> SEQ ID NO 42
<211> LENGTH: 42
<212> TYPE: DNA
<213> ORGANISM: Artificial Sequence
<220> FEATURE:
<223> OTHER INFORMATION: Primer

<400> SEQUENCE: 42
cccctaggtt aaaaggcaaa gacctgatcc tcaagtttgc tg                 42

<210> SEQ ID NO 43
<211> LENGTH: 40
<212> TYPE: DNA
<213> ORGANISM: Artificial Sequence
<220> FEATURE:
<223> OTHER INFORMATION: Primer

<400> SEQUENCE: 43
cgtggatccc acaatggcct ttccatgggc agataagtgg                    40

<210> SEQ ID NO 44
<211> LENGTH: 39
<212> TYPE: DNA
<213> ORGANISM: Artificial Sequence
<220> FEATURE:
<223> OTHER INFORMATION: Primer

<400> SEQUENCE: 44
cccctaggtt acttggtctt gatggtgtcc ttcttcacc                     39

<210> SEQ ID NO 45
<211> LENGTH: 49
<212> TYPE: DNA
<213> ORGANISM: Artificial Sequence
<220> FEATURE:
<223> OTHER INFORMATION: Primer

<400> SEQUENCE: 45
cgtggatccc acaatgctta tcaaggaatc ctaccacgac gtcaaaacc         49

<210> SEQ ID NO 46
<211> LENGTH: 36
<212> TYPE: DNA
<213> ORGANISM: Artificial Sequence
<220> FEATURE:
<223> OTHER INFORMATION: Primer

<400> SEQUENCE: 46
cccctaggct aacaaacgtc ctcgaccttc tcctcg                      36

<210> SEQ ID NO 47
<211> LENGTH: 43
<212> TYPE: DNA
<213> ORGANISM: Artificial Sequence
<220> FEATURE:
<223> OTHER INFORMATION: Primer

<400> SEQUENCE: 47
cgtggatccc acaatgaaat acgcagagga ccacaacggc tac              43

<210> SEQ ID NO 48
<211> LENGTH: 35
<212> TYPE: DNA
<213> ORGANISM: Artificial Sequence
<220> FEATURE:
<223> OTHER INFORMATION: Primer

<400> SEQUENCE: 48
cccctaggct aatccagctt gttgacccgg tcgct                       35

<210> SEQ ID NO 49
<211> LENGTH: 476
<212> TYPE: PRT
<213> ORGANISM: Artificial Sequence
<220> FEATURE:
<223> OTHER INFORMATION: Chimeric protein between CpFAD2 and CpFAH12

<400> SEQUENCE: 49

Met Ala Ala Ala Thr Ser Ala Met Pro Lys Asn Ser Val Leu Arg Arg
1               5                   10                  15

Thr Ala Ala Ser Thr Asn Ala Asn Asp Tyr Glu Ser Ser Ala Ala Val
            20                  25                  30

Ser Pro Ala Asp Ser Pro Arg Pro Ser Ala Ser Ser Thr Ser Leu Ser
        35                  40                  45

Ser Leu Ser Ser Leu Asp Ala Asn Asp Lys Lys Asp Glu Tyr Ala Gly
    50                  55                  60

Leu Leu Asp Thr Tyr Gly Asn Ala Phe Thr Pro Asp Phe Thr Ile
65                  70                  75                  80

Lys Asp Ile Arg Asp Ala Ile Pro Lys His Cys Tyr Glu Arg Ser Ala
                85                  90                  95

Leu Lys Gly Tyr Gly Tyr Ile Leu Arg Asp Ile Ala Cys Leu Ser Thr
            100                 105                 110

Thr Phe Tyr Leu Phe His Asn Phe Val Thr Pro Glu Asn Val Pro Ser
        115                 120                 125

Thr Pro Leu Arg Phe Ala Leu Trp Gly Ile Tyr Thr Val Leu Gln Gly
    130                 135                 140

Leu Phe Gly Thr Gly Leu Trp Val Ile Ala His Glu Cys Gly His Gly
145                 150                 155                 160

```
Ala Phe Ser Pro Ser Thr Leu Ile Asn Asp Val Thr Gly Trp Val Leu
                165                 170                 175

His Ser Ala Leu Leu Val Pro Tyr Phe Ser Trp Lys Phe Ser His Ser
            180                 185                 190

Ala His His Lys Gly Ile Gly Asn Met Glu Arg Asp Met Val Phe Leu
        195                 200                 205

Pro Arg Thr Arg Glu Gln Gln Ala Thr Arg Leu Gly Arg Ala Val Glu
    210                 215                 220

Glu Leu Gly Asp Leu Cys Glu Glu Thr Pro Ile Tyr Thr Ala Leu His
225                 230                 235                 240

Leu Val Gly Gln Gln Leu Ile Gly Trp Pro Ser Tyr Leu Met Ala Asn
                245                 250                 255

Val Thr Gly His Asn Phe His Glu Arg Gln Arg Glu Gly Arg Gly Lys
            260                 265                 270

Gly Lys Lys Asn Gly Phe Gly Gly Ser Val Asn His Phe Asp Pro Arg
        275                 280                 285

Ser Pro Ile Phe Glu Ala Arg His Ala Lys Tyr Ile Val Leu Ser Asp
    290                 295                 300

Ile Gly Leu Gly Leu Ala Ile Ala Ala Leu Val Tyr Leu Gly Asn Arg
305                 310                 315                 320

Phe Gly Trp Ala Asn Met Ala Val Trp Tyr Phe Leu Pro Tyr Leu Trp
                325                 330                 335

Val Asn His Trp Leu Val Ala Ile Thr Phe Leu Gln His Thr Asp Pro
            340                 345                 350

Thr Leu Pro His Tyr Thr Ala Glu Glu Trp Asn Tyr Val Arg Gly Ala
        355                 360                 365

Ala Ala Thr Ile Asp Arg Glu Met Gly Phe Ile Gly Arg His Leu Leu
    370                 375                 380

His Gly Ile Ile Glu Thr His Val Leu His His Tyr Val Ser Ser Ile
385                 390                 395                 400

Pro Phe Tyr Asn Ala Asp Glu Ala Ser Glu Ala Ile Lys Pro Val Met
                405                 410                 415

Gly Lys His Tyr Arg Ser Glu Thr Lys Asp Gly Pro Val Gly Phe Ile
            420                 425                 430

Arg Ala Leu Trp Lys Thr Ala Arg Trp Cys Gln Trp Val Glu Pro Ser
        435                 440                 445

Ala Glu Ala Glu Gly Ala Gly Lys Gly Val Leu Phe Phe Arg Asn Arg
    450                 455                 460

Asn Gly Leu Gly Thr Lys Pro Ile Ser Met Lys Asn
465                 470                 475
```

<210> SEQ ID NO 50
<211> LENGTH: 476
<212> TYPE: PRT
<213> ORGANISM: Artificial Sequence
<220> FEATURE:
<223> OTHER INFORMATION: Chimeric protein between CpFAD2 and CpFAH12

<400> SEQUENCE: 50

```
Met Ala Ala Ala Thr Ser Ala Met Pro Lys Asn Ser Val Leu Arg Arg
1               5                   10                  15

Thr Ala Ala Ser Thr Asn Ala Asn Asp Tyr Glu Ser Ser Ala Ala Val
            20                  25                  30

Ser Pro Ala Asp Ser Pro Arg Pro Ser Ala Ser Ser Thr Ser Leu Ser
        35                  40                  45
```

-continued

```
Ser Leu Ser Ser Leu Asp Ala Asn Asp Lys Lys Asp Glu Tyr Ala Gly
 50                  55                  60
Leu Leu Asp Thr Tyr Gly Asn Ala Phe Thr Pro Pro Asp Phe Thr Ile
 65                  70                  75                  80
Lys Asp Ile Arg Asp Ala Ile Pro Lys His Cys Tyr Glu Arg Ser Ala
                 85                  90                  95
Leu Lys Gly Tyr Gly Tyr Ile Leu Arg Asp Ile Ala Cys Leu Ser Thr
                100                 105                 110
Thr Phe Tyr Leu Phe His Asn Phe Val Thr Pro Glu Asn Val Pro Ser
            115                 120                 125
Thr Pro Leu Arg Phe Ala Leu Trp Gly Ile Tyr Thr Val Leu Gln Gly
        130                 135                 140
Leu Phe Gly Thr Gly Leu Trp Val Ile Ala His Glu Cys Gly His Gly
145                 150                 155                 160
Ala Phe Ser Pro Ser Thr Leu Ile Asn Asp Val Thr Gly Trp Val Leu
                165                 170                 175
His Ser Ala Leu Leu Val Pro Tyr Phe Ser Trp Lys Phe Ser His Ser
            180                 185                 190
Ala His His Lys Gly Ile Gly Asn Met Glu Arg Asp Met Val Phe Leu
        195                 200                 205
Pro Arg Thr Arg Glu Gln Gln Ala Thr Arg Leu Gly Arg Ala Val Glu
210                 215                 220
Glu Leu Gly Asp Leu Cys Glu Glu Thr Pro Ile Tyr Thr Ala Leu His
225                 230                 235                 240
Leu Val Gly Gln Gln Leu Ile Gly Trp Pro Ser Tyr Leu Met Ala Asn
                245                 250                 255
Val Thr Gly His Asn Phe His Glu Arg Gln Arg Glu Gly Arg Gly Lys
            260                 265                 270
Gly Lys Lys Asn Gly Phe Gly Gly Ser Val Asn His Phe Asp Pro Arg
        275                 280                 285
Ser Pro Ile Phe Glu Ala Arg His Ala Lys Tyr Ile Val Leu Ser Asp
290                 295                 300
Ile Gly Leu Gly Leu Ala Ile Ala Ala Leu Val Tyr Leu Gly Asn Arg
305                 310                 315                 320
Phe Gly Trp Ala Asn Met Ala Val Trp Tyr Phe Leu Pro Tyr Leu Trp
                325                 330                 335
Val Asn His Trp Leu Val Ala Ile Thr Phe Leu Gln His Thr Asp Pro
            340                 345                 350
Thr Leu Pro His Tyr Asn Arg Glu Glu Trp Asn Phe Val Arg Gly Gly
        355                 360                 365
Ala Cys Thr Ile Asp Arg Asp Leu Gly Phe Ile Gly Arg His Leu Phe
370                 375                 380
His Gly Ile Ala Asp Thr His Val Val His His Tyr Val Ser Arg Ile
385                 390                 395                 400
Pro Phe Tyr Asn Ala Asp Glu Ala Ser Glu Ala Ile Lys Pro Ile Met
                405                 410                 415
Gly Lys His Tyr Arg Ser Asp Thr Ala His Gly Pro Val Gly Phe Leu
            420                 425                 430
His Ala Leu Trp Lys Thr Ala Arg Trp Cys Gln Trp Val Glu Pro Ser
        435                 440                 445
```

```
Ala Glu Ala Glu Gly Ala Gly Lys Gly Val Leu Phe Phe Arg Asn Arg
        450                 455                 460

Asn Gly Leu Gly Thr Lys Pro Ile Ser Met Lys Asn
465                 470                 475

<210> SEQ ID NO 51
<211> LENGTH: 477
<212> TYPE: PRT
<213> ORGANISM: Artificial Sequence
<220> FEATURE:
<223> OTHER INFORMATION: Chimeric protein between CpFAD2 and CpFAH12

<400> SEQUENCE: 51

Met Ala Ala Ala Thr Ser Ala Met Pro Lys Asn Ser Val Leu Arg Arg
1               5                   10                  15

Thr Ala Ala Ser Thr Asn Ala Asn Asp Tyr Glu Ser Ser Ala Ala Val
            20                  25                  30

Ser Pro Ala Asp Ser Pro Arg Pro Ser Ala Ser Ser Thr Ser Leu Ser
        35                  40                  45

Ser Leu Ser Ser Leu Asp Ala Asn Asp Lys Lys Asp Glu Tyr Ala Gly
    50                  55                  60

Leu Leu Asp Thr Tyr Gly Asn Ala Phe Thr Pro Pro Asp Phe Thr Ile
65                  70                  75                  80

Lys Asp Ile Arg Asp Ala Ile Pro Lys His Cys Tyr Glu Arg Ser Ala
                85                  90                  95

Leu Lys Gly Tyr Gly Tyr Ile Leu Arg Asp Ile Ala Cys Leu Ser Thr
            100                 105                 110

Thr Phe Tyr Leu Phe His Asn Phe Val Thr Pro Glu Asn Val Pro Ser
        115                 120                 125

Thr Pro Leu Arg Phe Ala Leu Trp Gly Ile Tyr Thr Val Leu Gln Gly
    130                 135                 140

Leu Phe Gly Thr Gly Leu Trp Val Ile Ala His Glu Cys Gly His Gly
145                 150                 155                 160

Ala Phe Ser Pro Ser Thr Leu Ile Asn Asp Val Thr Gly Trp Val Leu
                165                 170                 175

His Ser Ala Leu Leu Val Pro Tyr Phe Ser Trp Lys Phe Ser His Ser
            180                 185                 190

Ala His His Lys Gly Ile Gly Asn Met Glu Arg Asp Met Val Phe Leu
        195                 200                 205

Pro Arg Thr Arg Glu Gln Gln Ala Thr Arg Leu Gly Arg Ala Val Glu
    210                 215                 220

Glu Leu Gly Asp Leu Cys Glu Glu Thr Pro Ile Tyr Thr Ala Leu His
225                 230                 235                 240

Leu Val Gly Gln Gln Leu Ile Gly Trp Pro Ser Tyr Leu Met Ala Asn
                245                 250                 255

Val Thr Gly His Asn Phe His Glu Arg Gln Arg Glu Gly Arg Gly Lys
            260                 265                 270

Gly Lys Lys Asn Gly Phe Gly Gly Ser Val Asn His Phe Asp Pro Arg
        275                 280                 285

Ser Pro Ile Phe Glu Ala Arg His Ala Lys Tyr Ile Val Leu Ser Asp
    290                 295                 300

Ile Gly Leu Gly Leu Ala Ile Ala Ala Leu Val Tyr Leu Gly Asn Arg
305                 310                 315                 320

Phe Gly Trp Ala Asn Met Ala Val Trp Tyr Phe Leu Pro Tyr Leu Trp
                325                 330                 335
```

```
Val Asn His Trp Leu Val Ala Ile Thr Phe Leu Gln His Thr Asp Pro
            340                 345                 350

Thr Leu Pro His Tyr Asn Arg Glu Glu Trp Asn Phe Val Arg Gly Gly
        355                 360                 365

Ala Cys Thr Ile Asp Arg Asp Leu Gly Phe Ile Gly Arg His Leu Phe
    370                 375                 380

His Gly Ile Ala Asp Thr His Val Val His His Tyr Val Ser Arg Ile
385                 390                 395                 400

Pro Phe Tyr Asn Ala Asp Glu Ala Ser Glu Ala Ile Lys Pro Ile Met
                405                 410                 415

Gly Lys His Tyr Arg Ser Asp Thr Ala His Gly Pro Val Gly Phe Leu
            420                 425                 430

His Ala Leu Trp Lys Thr Ala Arg Trp Cys Gln Trp Val Glu Pro Ser
            435                 440                 445

Ala Asp Ala Gln Gly Ala Gly Lys Gly Ile Leu Phe Tyr Arg Asn Arg
        450                 455                 460

Asn Lys Leu Gly Thr Lys Pro Ile Ser Met Lys Thr Gln
465                 470                 475
```

MUTANT YEASTS CAPABLE OF PRODUCING AN UNUSUAL FATTY ACID

CROSS-REFERENCE TO RELATED APPLICATIONS

This application is a U.S. National Stage Application under 35 U.S.C. § 371 of International Application No. PCT/IB2014/061116, filed Apr. 30, 2014, which claims the benefit of and priority to French Patent Application No. 1354062, filed May 2, 2013. Each of these applications is hereby incorporated by reference in its entirety.

A computer readable text file, entitled "SequenceListing," created on or about Nov. 2, 2015 with a file size of about 28 kb contains the sequence listing for this application and is hereby incorporated by reference in its entirety.

The present invention relates to mutant yeasts capable of producing an unusual fatty acid by bioconversion or by neosynthesis and to the use of these yeasts for producing this unusual fatty acid.

Industrial fatty acids come mainly from mineral oils or vegetable oils. These industrial fatty acids are intended for various applications, such as food, paints and varnishes, lubricants, impermeabilizing agents, plastics and polymers. They can have very diverse structures, for example polyunsaturated fatty acids, with very short or very long chains, having hydroxyl or epoxy groups, or having one or more conjugated double or triple bonds. The cost of obtaining industrial fatty acids from mineral oils is high because of the increasingly high cost of the raw material and the cost of chemically treating these mineral oils. Certain plant species produce fatty acids with properties that are advantageous in the industrial field, but these species are generally wild, exotic and/or non-agronomic species.

The use of microorganisms, in particular yeast strains, for the production of industrial fatty acids represents an alternative to the use of fossil and plant resources.

In a yeast, an unusual fatty acid is a fatty acid which is not naturally synthesized by said yeast.

Ricinoleic acid (12-hydroxy-9-cis-octadecenoic acid; C18:1-OH) is an omega-9 hydroxylated fatty acid, which is unusual in yeasts. Ricinoleic acid (RA) and derivatives thereof have several industrial applications, for example in the food industry as additives, the textile industry as surfactants or pigment wetting agents, the paper industry as antifoams or impermeabilizing additives, the plastics industry for the manufacture of nylon-11, plasticizers, tubes or films, fragrances and cosmetics as emulsifiers or deodorants, the electronics industry for the manufacture of condenser fluids, polyurethane or polyamide resins, pharmaceutical products, paints, inks, adhesives and lubricants. More recently, ricinoleic acid has been proposed as a constituent of biodiesel and as a lubricating additive for replacing sulfur-based lubricating compounds in petroleum diesel.

Ricinoleic acid represents approximately 90% of the total fatty acids of the seeds of the castor oil plant (*Ricinus communis*) (Yamamoto et al., 2008). The high ricinoleic acid content in castor oil, combined with a high oil content in the seeds of the castor oil plant and with the multitude of applications of ricinoleic acid, make the castor oil plant an oleaginous crop with a high economic value. However, a main drawback to the extensive cultivation of the castor plant is the high content in its seeds of ricin, an extremely toxic protein (Knight, 1979). The use of ricin has for a long time raised public health worries. Because of legislation regarding health, most of the ricinoleic acid supply to western countries is based on the importation of castor oil from developing countries, in which the economic instability often leads to fluctuations in the availability, the quality and the price of the oil (Chan et al., 2010).

Not many alternative sources to the castor oil plant exist for producing ricinoleic acid. The only species known to produce significant amounts of ricinoleic acid is *Claviceps purpurea*—rye ergot—which accumulates ricinoleic acid in its sclerotia up to an amount of 23% of its total lipids (Meesapyodsuk et al., 2008). By way of comparison, cotton, soybean and *Lesquerella* species produce ricinoleic acid in an amount of 0.27%, 0.03% and 0.3% of their total lipids, respectively (Yamamoto et al., 2008).

The limited amount of natural sources of ricinoleic acid has led chemists to develop methods for preparing hydroxy fatty acids from commercial vegetable oils (Dahlke B et al., 1995). In parallel, considerable genetic engineering efforts have been made to produce ricinoleic acid in the seeds of the model plant *Arabidopsis thaliana* and in the model yeasts *Saccharomyces cerevisiae* and *Schizosaccharomyces pombe*. However, these yeasts are not oleaginous yeasts, i.e. they do not have the capacity to accumulate large amounts of lipids. The strategy of genetic engineering these model species consists of a heterologous expression of the oleate (Δ12) hydroxylase of the castor oil plant or of *Claviceps purpurea*, encoding the FAH12 gene. This is because, during the biosynthesis of ricinoleic acid, oleic acid is hydroxylated by the Fah12p enzyme in the sn-2 position of mainly phosphatidylcholine principally, in the endoplasmic reticulum (Bafor et al., 1991). The hydroxylation is carried out at position 12 of the esterified oleic acid.

Oleate desaturases and oleate hydroxylases belong to the same family of membrane proteins and have a similar peptide sequence and a similar function. They share the same oleic substrate and their reactions are very competitive (Broun et al., 1998). Oleate (Δ12) desaturase (FAD2) preferentially forms linoleic acid and oleate hydroxylase preferentially forms oleic acid.

For the production of ricinoleic acid in *A. thaliana*, it has therefore been proposed to delete the gene encoding oleate (Δ12) desaturase before the expression of oleate (Δ12) hydroxylase. However, the transgenic expression of the oleate (Δ12) hydroxylase of *Ricinus communis* (RcFAH12) results in the accumulation of ricinoleic acid and of other hydroxylated fatty acids in an amount of only 15-20% of the total fatty acids in the *A. thaliana* seeds (Broun and Somerville, 1997; Smith et al., 2003). The transgenic coexpression of RcFAH12 and of acyl-CoA:diacylglycerol acyl transferase of *Ricinus communis* (RcDGAT2) results in an increase in the accumulation of hydroxylated fatty acids up to 30% of the total fatty acids in the seeds, but this represents a content that is still lower than that which is found in the seeds of the castor oil plant (Lu et al., 2006; Burgal et al., 2008). It is nevertheless necessary to overexpress at least one acyl-CoA:diacylglycerol acyl transferase (DGA) in these genetically modified *A. thaliana* plants in order to increase ricinoleic acid production. For the production of ricinoleic acid in the yeasts *S. cerevisiae* and *S. pombe*—which do not contain genes encoding oleate (Δ12) desaturases—the heterologous expression of the oleate (Δ12) hydroxylase of *C. purpurea* (CpFAH12) results in an accumulation of ricinoleic acid in an amount respectively of 8% and 53% of the total fatty acids (Mavraganis et al., 2010; Holic et al., 2012). In *S. cerevisiae*, when the acyl-CoA:diacylglycerol acyl transferase of *C. purpurea* (CpDGAT2) is coexpressed with RcFAH12, the ricinoleic acid content increases slightly up to 10% of the total fatty acids (Mavraganis et al., 2010). Nevertheless, the total lipids in these yeasts represents only approximately 5% of the cell dry weight (CDW). These mutant yeasts cannot therefore be considered to be alternative solutions to the production of ricinoleic acid. It should be noted that it is not necessary to inhibit the beta-oxidation of the fatty acids of these genetically modified *S. cerevisiae* and *S. pombe* yeasts in order for said yeasts to produce ricinoleic acid. These results show that the transgenic expression of an oleate (Δ12) hydroxylase alone or in combination with an acyl transferase specific for ricinoleic acid (DGAT2) in *A. thaliana* and the yeasts is not sufficient to produce ricinoleic acid at a high content as is found in castor oil.

There is therefore a need to obtain mutant organisms capable of accumulating amounts of ricinoleic acid that are comparable to those that are found in the castor oil plant.

Vernolic acid (12,13-epoxy-9-cis-octadecenoic acid; $C_{18}H_{32}O_3$) is an omega-9 epoxidized fatty acid, which is also unusual in yeasts. Vernolic acid has several industrial applications, for example in adhesives, paints, plastics, inks, the textile industry and the pharmaceutical industry. Vernolic acid represents at least 60% of the total fatty acids of the seeds of *Vernonia galamensis* and of *Euphorbia lagascae*.

Certain oleaginous microorganisms are capable of converting substrates, such as fats, sugars or glycerol, into lipids, in particular into triglycerides and fatty acids. These oleaginous microorganisms have the capacity to accumulate large amounts of lipids, in an amount of at least 20% of their solids content. In yeasts, several oleaginous species, termed non-conventional, are found, among which mention may be made of those belonging to the genera *Candida, Cryptococus, Lipomyces, Rhodosporidium, Rhodotorula, Trichosporon* or *Yarrowia* (for reviews, see Beopoulos et al., 2009; Papanikolaou et al., 2011a and 2011b).

*Yarrowia lipolytica* is a hemiascomycete yeast. It is considered to be a model of bioconversion for the production of proteins, enzymes and lipid derivatives (for review, see Nicaud, 2012). It is naturally present in environments polluted with petroleum and in particular in the heavy fractions. *Y. lipolytica* is one of the oleaginous yeasts that has been most studied owing not only to its capacity to accumulate lipids in an amount of more than 50% of its solids content according to a defined culture profile, or even more than 80% of its solids content when appropriate genetic modifications are made, but also of its unique capacity to accumulate linoleic acid at high levels (more than 50% of the fatty acids produced under certain culture conditions) and also lipids with a high added value, such as stearic acid, palmitic acid and oleic acid (Papanikolaou et al., 2001; Beopoulos et al. 2008; Papanikolaou et al., 2010; Dulermo and Nicaud 2011). *Y. lipolytica* is also capable of accumulating more than 90% of neutral lipids, in the form of triacylglycerols (TAGs). *Y. lipolytica* can be efficiently cultured on a large variety of hydrophobic compounds (free fatty acids, triacylglycerols, n-alkanes, etc.) as sole carbon and energy source, through the expression of multigene families encoding key enzymes involved in the decomposition of these compounds (e.g., acyl-CoA oxidases, lipases) (Papanikolaou et al., 2001; Beopoulos et al., 2009a; Papanikolaou et al., 2010; 2011a and 2011b). The lipid synthesis in *Y. lipolytica* is carried out either by de novo biosynthesis of fatty acids via the production of fatty acid precursors such as acetyl-CoA and malonyl-CoA and the integration thereof into the lipid biosynthesis pathway (Kennedy pathway), or by the ex novo accumulation, via the incorporation of the fatty acids preexisting in the fermentation medium or deriving from the hydrolysis of the oils, fats, triglycerides and methyl esters of the culture medium and accumulation thereof inside the cell. The main lipid de novo biosynthesis pathways in *Y. lipolytica* and *Saccharomyces cerevisiae* (*S. cerevisiae*; yeast termed non-oleaginous) are well conserved. The genes involved in fatty acid metabolism in yeasts, in particular *Y. lipolytica*, are described in Beopoulos et al. (2009) and International application WO 2010/004141.

In yeasts, β-oxidation is a fatty acid degradation pathway which is located solely in the peroxisomes. This pathway enables the formation of acetyl-CoA from even-chain fatty acids and of propionyl-CoA from odd-chain fatty acids. β-Oxidation comprises four successive reactions during which the carbon chain of acyl-CoA is reduced by two carbon atoms. Once the reaction has taken place, the acyl-CoA reduced by two carbons can return to the β-oxidation spiral (Lynen helix) and undergoes a further reduction by two carbons. These decarboxylation cycles can be interrupted depending on the nature of the acyl-CoA, the substrate availability, the presence of coenzyme A or of acetyl-CoA, or according to the $NAD^+/NADH$ ratio. In the first step of the β-oxidation, after the release of the fatty acids from the triacylglycerols (TAGs) by the lipases, the active form of acyl-CoA formed is oxidized by a flavin adenine dinucleotide (FAD) molecule so as to form a trans-$\Delta^2$-enoyl-CoA molecule by means of an acyl-CoA oxidase (AOX). The β-oxidation in *Y. lipolytica* has been widely described (Wang et al., 1999b; Mlickova et al. 2004). There are 6 acyl-CoA oxidases in *Y. lipolytica*, encoded by the POX1 to 6 genes, which have different substrate specificities (Wang et al., 1999a and 1999b; Luo et al., 2000 and 2002). The trans-$\Delta^2$-enoyl-CoA is then hydrated by 2-enoyl-CoA hydratase. The 3-hydroxyacyl CoA molecule formed is oxidized by $NAD^+$ so as to form a 3-ketoacyl-CoA molecule. These last two steps are catalyzed by a bifunctional protein encoded by the MFE1 gene (multifunctional enzyme which has a 3-hydroxyacyl-CoA dehydrogenase function). The 3-oxoacyl-CoA thioester is then cleaved by a 3-oxoacyl-CoA thiolase encoded by the POT1 gene (Einerhand et al., 1995). A coenzyme A is then added so as to form an acetyl-CoA and an acyl-CoA reduced by two carbons. Mutant *Y. lipolytica* strains in which the fatty acid beta-oxidation is knocked out because of the deletion of the 6 endogenous POX genes have been described by Beopoulos et al. (2008) and in International application WO 2012/001144. These mutant strains exhibit an increased lipid accumulation compared with the parent strains.

Moreover, *Y. lipolytica* is currently used for the industrial conversion of ricinoleic acid to γ-decalactone, an aromatic compound with fruity and oily notes which can be found naturally in fermented foods and fruits (Schrader et al., 2004).

In the context of their research, the inventors have obtained a genetically modified mutant *Yarrowia lipolytica* yeast strain which can be of use as a template yeast strain for obtaining other mutant *Y. lipolytica* strains capable of producing unusual omega-9 fatty acids. In this genetically modified *Y. lipolytica* strain, the endogenous oleate (Δ12) desaturase (encoded by the FAD2 gene) has been knocked out in order to prevent the conversion of oleic acid to linoleic acid. The β-oxidation pathway, responsible for the degradation of lipid stores, has been abolished by the deletion of the 6 POX genes encoding the 6 endogenous acyl-CoA oxidases (AOX1 to AOX6). The accessibility of the oleic substrate in phospholipid form for an enzyme (for example a hydroxylase or an epoxidase) has been facilitated by the knockout of the 3 genes encoding the endogenous triacylglycerol acyl transferases (DGA1, DGA2, LRO1), in order to prevent the storage of oleic acid in TAG form. This mutant template *Y.*

*lipolytica* strain containing the 10 genetic modifications pox1-6Δ,dga1Δ,dga2Δ,lro1Δfad2Δ is called JMY2159. It is incapable of degrading oleic acid, of storing it in triglyceride form and of converting it by desaturation to linoleic acid.

From this JMY2159 template strain, the inventors have subsequently obtained genetically modified mutant *Y. lipolytica* yeast strains having a considerable capacity to accumulate lipids and capable of synthesizing ricinoleic acid up to more than 7% of their solids content. The heterologous expression, in the JMY2159 template strain, of a nucleotide sequence encoding the *Ricinus communis* oleate (Δ12) hydroxylase (RcFAH12), under the control of the TEF constitutive promoter, has made it possible to obtain a mutant strain (called JMY2331) which produces ricinoleic acid in an amount of 7% of its total lipids. The heterologous expression, in the JMY2159 template strain, of one or of two nucleotide sequences encoding the *Claviceps purpurea* oleate (Δ12) hydroxylase (CpFAH12), respectively under the control of the TEF constitutive promoter, has given rise to mutant strains (called JMY2324 and JMY2511 respectively) capable of accumulating ricinoleic acid in an amount of 29% and 35%, respectively, of their total lipids. The overexpression, in a strain similar to the JMY2511 strain (in which the two nucleotide sequences encoding CpFAH12 are respectively under the control of the TEF promoter; JMY2527 strain), of the endogenous phospholipid:diacylglycerol acyl transferase (PDAT) encoded by the YlLRO1 gene, which is an enzyme capable of catalyzing the formation of triacylglycerol from 1,2-sn-diacylglycerol, makes it possible to achieve an accumulation of ricinoleic acid in the mutant strain thus obtained (called JMY2556 or JMY2853 depending of the auxotrophies of the strain) in an amount of 42% of its total lipids. This level of ricinoleic acid production by the JMY2556 strain can be further increased by increasing the number of copies of the CpFAH12 and YlLRO1 genes, or by inhibiting the expression of the endogenous 2-methylcitrate dehydratase of the strain and/or by overexpressing one or more of the following endogenous enzymes of said strain: monoacylglycerol acyl transferase, patatin-like triacylglycerol lipase, at least one of the two subunits of ATP citrate lyase, diacylglycerol:choline-O phosphotransferase, ethanolamine phosphotransferase, phospholipase $A_2$, an acyl-CoA:lysophosphatidylcholine acyl transferase, a cytochrome-$b_5$ reductase, inositol/phosphatidyl inositol phosphatase and elongase.

In addition, surprisingly, the genetically modified mutant *Y. lipolytica* yeast strains capable of synthesizing ricinoleic acid (in particular the JMY3030 strain) are also capable of secreting it. This property of these mutant strains has an advantage for the production of ricinoleic acid in large amount (it is not necessary to lyse the cells in order to obtain the ricinoleic acid).

The genetic modifications carried out in *Yarrowia lipolytica* can also be carried out in the other oleaginous yeasts. These mutant oleaginous yeast strains can be used as alternatives to the production of ricinoleic acid by the castor oil plant, insofar as they are easy to culture, this being independently of the seasons and of the climate.

A subject of the present invention is therefore a method for obtaining a mutant oleaginous yeast strain which is of use as a template yeast strain for obtaining other mutant oleaginous yeast strains, comprising:
(a) the inhibition of fatty acid beta-oxidation in said strain,
(b) the inhibition of the expression or of the activity of one or more of the endogenous acyl-CoA:diacylglycerol acyl transferases (DGATs) of said strain, preferably of all the endogenous DGATs of said strain,
(c) the inhibition of the expression or of the activity of the endogenous oleate desaturase (FAD2) of said strain, and optionally
(d) the inhibition of the expression or of the activity of an endogenous phospholipid:diacylglycerol acyl transferase (PDAT) of said strain.

Steps (a) to (d) of the method according to the invention can be carried out in any order, simultaneously or sequentially.

According to one advantageous embodiment of this method, the inhibition of the fatty acid beta-oxidation defined in step (a) above is obtained by:
the inhibition of the expression or of the activity of the endogenous acyl-CoA oxidases (AOXs) of said strain and/or
the inhibition of the expression or of the activity of the endogenous multifunctional enzyme having the 3-hydroxyacyl-CoA dehydrogenase and enoyl-CoA hydratase activities of said strain and/or
the inhibition of the expression or of the activity of the endogenous 3-oxoacyl-CoA thiolase of said strain.

The oleaginous yeast strains are well known to those skilled in the art. They have the capacity to accumulate large amounts of lipids, in an amount of at least 20% of their solids content (Ratledge, 1994). They generally belong to the genus *Candida*, *Cryptoccocus*, *Lipomyces*, *Rhodosporidium* (e.g., *Rhodosporidium toruloides*), *Rhodotorula* (e.g., *Rhodotura glutinis*), *Trichosporon* or *Yarrowia*.

The genomes of *Lipomyces* and of *Rhodosporidium* have been sequenced: for *Lipomyces starkeyi*, see the Joint Genome Institute (JGI) and for *Rhodosporidium toruloides*, see Kumar et al. (2012) and Zhu et al. (2012).

A strain which is more particularly preferred for the purposes of the present invention is a *Yarrowia* yeast strain, more preferably a *Yarrowia lipolytica* yeast strain.

The term "template yeast strain" is intended to mean a yeast strain from which other genetic modifications can be carried out in said strain.

The inhibition of the expression or of the activity of an enzyme defined in the present invention may be total or partial. It may be obtained in various ways by methods known in themselves to those skilled in the art.

Advantageously, this inhibition may be obtained by mutagenesis of the gene encoding said enzyme.

The mutagenesis of the gene encoding said enzyme can take place at the level of the coding sequence or of the sequences for regulating the expression of this gene, in particular at the level of the promoter, resulting in an inhibition of transcription or of translation of said enzyme.

The mutagenesis of the gene encoding said enzyme can be carried out by genetic engineering. It is, for example, possible to delete all or part of said gene and/or to insert an exogenous sequence. Methods which made it possible to delete (eliminate) or insert a given genetic sequence in the yeast, in particular *Y. lipolytica*, are well known to those skilled in the art (for review, see Barth and Gaillardin, 1996; Madzak et al., 2004). By way of example, use may be made of the method referred to as POP IN/POP OUT which has been used in yeasts, in particular in *Y. lipolytica*, for deleting the LEU2, URA3 and XPR2 genes (Barth and Gaillardin, 1996). Use may also be made of the SEP method (Maftahi et al., 1996) which has been adapted in *Y. lipolytica* for deleting the POX genes (Wang et al., 1999b). Advantageously, use may also be made of the SEP/Cre method developed by Fickers et al. (2003) and described in International application WO 2006/064131. In addition, methods which make it possible to inhibit the expression or the activity of an enzyme in yeasts are described in International application WO 2012/001144. An advantageous method according to the present invention consists in replacing the coding sequence of the gene encoding said enzyme with an expression cassette containing the sequence of a gene encoding a selectable marker. It is also possible to introduce one or more point mutations into the gene encoding said enzyme, resulting in a shift in the reading frame, and/or to introduce a stop codon into the sequence and/or to inhibit the transcription or the translation of the gene encoding said enzyme.

The mutagenesis of the gene encoding said enzyme can also be carried out using physical agents (for example radiation) or chemical agents. This mutagenesis also makes it possible to introduce one or more point mutations into the gene encoding said enzyme.

The mutated gene encoding said enzyme can be identified for example by PCR using primers specific for said gene.

It is possible to use any selection method known to those skilled in the art which is compatible with the marker gene (or genes) used. The selectable markers which enable the complementation of an auxotrophy, also commonly referred to as auxotrophic markers, are well known to those skilled in the art. The URA3 selectable marker is well known to those skilled in the art. More specifically, a yeast strain in which the URA3 gene (sequence available in the Genolevures database (http://genolevures.org/) under the name YALI0E26741g or the UniProt database under accession number Q12724), encoding orotidine-5'-phosphate decarboxylase, is inactivated (for example by deletion), will not be capable of growing on a medium not supplemented with uracil. The integration of the URA3 selectable marker into this yeast strain will then make it possible to restore the growth of this strain on a uracil-free medium. The LEU2 selectable marker described in particular in patent U.S. Pat. No. 4,937,189 is also well known to those skilled in the art. More specifically, a yeast strain in which the LEU2 gene (YALI0C00407g), encoding 0-isopropylmalate dehydrogenase, is inactivated (for example by deletion), will not be capable of growing on a medium not supplemented with leucine. As previously, the integration of the LEU2 selectable marker into this yeast strain will then make it possible to restore the growth of this strain on a medium not supplemented with leucine. The ADE2 selectable marker is also well known to those skilled in the art in the field of yeast transformation. A yeast strain in which the ADE2 gene (YALI0B23188g), encoding phosphoribosylaminoimidazole carboxylase, is inactivated (for example by deletion), will not be capable of growing on a medium not supplemented with adenine. Here again, the integration of the ADE2 selectable marker into this yeast strain will then make it possible to restore the growth of this strain on a medium not supplemented with adenine. Leu$^-$ Ura$^-$ auxotrophic *Y. lipolytica* strains have been described by Barth and Gaillardin, 1996.

Advantageously, said mutant yeast strain is auxotrophic for leucine (Leu$^-$) and optionally for orotidine-5'-phosphate decarboxylase (Ura$^-$).

In yeasts, the 6 genes POX1, POX2, POX3, POX4, POX5 and POX6 encode 6 isoforms of acyl-coenzymeA oxidases (AOXs; E.C. 6.2.1.3) involved, at least partially, in fatty acid β-oxidation. The partial or total inhibition of the expression or of the activity of these isoenzymes results in the accumulation, by yeasts, of dodecanedioic acid, without consumption of the accumulated lipids. More particularly, the coding sequence of the POX1-6 genes and the peptide sequence of AOX1-6 of *Y. lipolytica* CLIB122 are available in the Génolevures database (genolevures.org/) or GenBank database under the following accession numbers or names: POX1/AOX1=YALI0E32835g/YALI0E32835p, POX2/AOX2=YALI0F10857g/YALI0F10857p; POX3/AOX3=YALI0D24750g/YALI0D24750p; POX4/AOX4=YALI0E27654g/YALI0E27654p; POX5/AOX5=YALI0C23859g/YALI0C23859p; POX6/AOX6=YALI0E06567g/YALI0E06567p. The peptide sequences of the acyl-CoA oxidases of *Y. lipolytica* exhibit 45% identity or 50% similarity with those of the other yeasts. The degree of identity between the acyl-CoA oxidases ranges from 55% to 70% (or 65% to 76% similarity) (International application WO 2006/064131). A method for inhibiting the expression of the 6 endogenous AOXs in a *Y. lipolytica* strain has been described in International applications WO 2006/064131, WO 2010/004141 and WO 2012/001144.

In yeasts, the multifunctional enzyme has three domains: two domains having a 3-hydroxyacyl-CoA dehydrogenase activity (E.C. 4.2.1.74; domains A and B) and one domain having an enoyl-CoA hydratase activity (E.C. 4.2.1.17; domain C). This enzyme is encoded by the MFE1 ("Multifunctional enzyme type 1") gene. More particularly, the coding sequence of the MFE1 gene and the peptide sequence of the 3-hydroxyacyl-CoA dehydrogenase and enoyl-CoA hydratase of *Y. lipolytica* CLIB122 are available in the Génolevures or GenBank databases under the following accession number or name: YALI0E15378g/YALI0E15378p. A method for inhibiting the expression of said endogenous multifunctional enzyme in a *Y. lipolytica* strain has been described by Haddouche et al. (2011).

In yeasts, the 3-oxoacyl-coenzyme A thiolase (E.C. 2.3.1.16) is encoded by the POT1 ("Peroxisomal Oxoacyl Thiolase 1") gene. More particularly, the coding sequence of the POT1 gene and the peptide sequence of the 3-oxoacyl-CoA thiolase of *Y. lipolytica* CLIB122 are available in the Génolevures or GenBank databases under the following accession number or name: YALI018568g/YALI018568p. A method for inhibiting the expression of the endogenous 3-oxoacyl-coenzyme A thiolase in a *Y. lipolytica* strain has been described by Berninger et al. (1993).

In yeasts, the acyl-CoA:diacylglycerol acyl transferases (DGAT; E.C. 2.3.1.20) are encoded by two genes: DGA1 and DGA2 (Beopoulos et al., 2009 and 2012; International application WO 2012/001144). More particularly, the coding sequence of the DGA1 gene and the peptide sequence of the acyl-CoA:diacylglycerol acyl transferase 1 of *Y. lipolytica* CLIB122 are available in the Génolevures or GenBank databases under the following accession number or name: YALI0E32769g/YALI0E32769p. The coding sequence of the DGA2 gene and the peptide sequence of the acyl-CoA:diacylglycerol acyl transferase 2 of *Y. lipolytica* CLIB122 are available in the Génolevures or GenBank databases under the following accession number or name: YALI0D07986g/YALI0D07986p. In *Rhodoturula glutanis*, an acyl-CoA:diacylglycerol acyl transferase has been described by Rani et al. (2013). A method for inhibiting the expression of one of or both the 2 endogenous DGATs (DGAT1 and/or DGAT2) in a *Y. lipolytica* strain has been described by Beopoulos et al. (2012).

Some yeasts naturally possess a gene encoding an oleate (Δ12) desaturase (E.C. 1.14.19.6) which is encoded by the FAD2 gene. For example, *Y. lipolytica* possesses this gene, whereas *S. cerevisiae* (which is not considered to be an oleaginous yeast) does not possess it (Ratledge, 2004; Beopoulos et al., 2008). More particularly, the coding sequence of the FAD2 gene and the peptide sequence of the oleate (Δ12) desaturase of *Y. lipolytica* CLIB122 are available in the Génolevures or GenBank databases under the following accession number or name: YALI0B10153g/ YALI0B10153p. If the yeast strain does not possess a gene encoding an oleate (Δ12) desaturase, then step (c) of the method according to the present invention will not be carried out.

In yeasts, the phospholipid:diacylglycerol acyl transferase (PDAT; E.C. 2.3.1.158) is encoded by the LRO1 gene (Beopoulos et al., 2009 and 2012; International application WO 2012/001144). More particularly, the coding sequence of the LRO1 gene and the peptide sequence of the phospholipid:diacylglycerol acyl transferase of *Y. lipolytica* CLIB122 are available in the Génolevures or GenBank databases under the following accession number or name: YALI0E6797g/YALI0E6797p. A method for inhibiting the endogenous PDAT in a *Y lipolytica* strain has been described by Beopoulos et al. (2012).

A subject of the present invention is also a method for obtaining a mutant oleaginous yeast strain capable of synthesizing an unusual omega-9 fatty acid, comprising steps (a) to (c) defined above, optionally step (d) defined above, and in addition the expression in said strain of a heterologous enzyme having an oleate hydroxylase (E.C. 1.14.99.33) or oleate epoxidase (E.C. 1.14.99.-; Lee et al., 1998) activity.

Advantageously, these mutant oleaginous yeast strains capable of synthesizing an unusual omega-9 fatty acid are also capable of secreting said unusual omega-9 fatty acid.

The term "heterologous enzyme" is intended to mean an enzyme that oleaginous yeasts do not naturally possess. This may be an enzyme originating from any prokaryotic or eukaryotic organism.

Enzymes having an oleate hydroxylase or oleate epoxidase activity (Lee et al., 1998) are known to those skilled in the art. The use of a particular enzyme having a hydroxylase or epoxidase activity depends on the unusual omega-9 fatty acid that those skilled in the art wish to have the mutant oleaginous yeast strain produce.

According to one preferred embodiment of this method, the unusual omega-9 fatty acid is ricinoleic acid and said method comprises the expression, in said strain, of a heterologous enzyme having an oleate (Δ12) hydroxylase activity, such as an oleate (Δ12) hydroxylase (FAH12) or an oleate (Δ12) desaturase (FAD2) that has been mutated so that it has an oleate (Δ12) hydroxylase activity, preferably an oleate (Δ12) hydroxylase.

According to one advantageous embodiment of this method, said oleate (Δ12) hydroxylase is the oleate (Δ12) hydroxylase of *Ricinus communis* (RcFAH12) or originates from a fungus of the ascomycetes division, preferably of the family Clavicipitaceae, more preferably of the *Claviceps* genus and quite preferentially of the *Claviceps purpurea* species (CpFAH12).

The peptide sequence of the RcFAH12 enzyme is available in the GenBank database under accession number GI:187940238. A nucleotide sequence encoding RcFAH12, optimized for its expression in yeast, is represented by the sequence SEQ ID No. 21.

The peptide sequence of the CpFAH12 enzyme is available in the GenBank database under accession number GI:194271137. A nucleotide sequence encoding CpFAH12, optimized for its expression in yeast, is represented by the sequence SEQ ID No. 22.

The mutated oleate (Δ12) desaturase having an oleate (Δ12) hydroxylase activity can be obtained by exchange of an oleate (Δ12) desaturase domain with one or more domains of an oleate (Δ12) hydroxylase conferring the hydroxylase activity (domains H2 and/or H3), and/or by mutagenesis (e.g., substitution) of one or more amino acids of the oleate (Δ12) desaturase with one or more amino acids of an oleate (Δ12) desaturase conferring a hydroxylase activity. By way of example, in plants, mutated oleate desaturases having an oleate hydroxylase activity have been described by Broun et al. (1998) and Broadwater et al. (2002).

Advantageously, the mutated oleate (Δ12) desaturase comes from a fungus of the family Clavicipitaceae, more preferably of the *Claviceps* genus and more preferably of the *Claviceps purpurea* species (CpFAD2; Meesapyodsuk et al., 2007), or comes from a yeast of the hemiascomycete family, preferably of the *Yarrowia* genus and more preferably of the *Yarrowia lipolytica* species (YlFAD2: YALI0B10153g/ YALI0B10153p).

In *C. purpurea*, the amino acid sequence of the oleate desaturase (CpFAD2) has 86% identity with the amino acid sequence of the oleate hydroxylase (CpFAH12). The difference in function between the desaturase and the hydroxylase of *C. purpurea* is therefore contained in the amino acids corresponding to the 14% of sequences which diverge between these 2 enzymes. Mutated CpFAD2s (chimeric proteins) having an oleate (Δ12) hydroxylase activity are represented as SEQ ID No. 49, 50 and 51, preferably SEQ ID No. 51.

The overexpression of an (endogenous, orthologous, heterologous) enzyme defined in the present invention in a mutant yeast strain according to the present invention can be obtained in various ways by methods known in themselves.

The overexpression of an enzyme defined in the present invention can be carried out by placing one or more (preferably two or three) copies of the open reading frame of the sequence encoding said enzyme under the control of appropriate regulatory sequences. Said regulatory sequences comprise promoter sequences, placed upstream (in 5') of the open reading frame of the sequence encoding said enzyme, and terminator sequences, placed downstream (in 3') of the open reading frame of the sequence encoding said enzyme.

Promoter sequences which can be used in the yeast are well known to those skilled in the art and can correspond in particular to inducible or constitutive promoters. By way of promoters which are usable in the method according to the present invention, mention may in particular be made of the promoter of a *Y. lipolytica* gene which is strongly repressed by glucose and which is inducible by fatty acids or triglycerides, such as the POX2 promoter of the acyl CoA oxidase 2 (AOX2) gene of *Y. lipolytica* and the LIP2 gene promoter described in International application WO 01/83773. Use may also be made of the promoter of the FBA1 gene encoding fructose-bisphosphate aldolase (application US 2005/0130280), the promoter of the GPM gene encoding phosphoglycerate mutase (International application WO 2006/0019297), the promoter of the YAT1 gene encoding the ammonium transporter (US 2006/0094102), the promoter of the GPAT gene encoding glyceryl-3-phosphate O-acyl transferase (application US 2006/0057690), the promoter of the TEF gene (Muller et al., 1998; application US 2001/ 6265185), the hp4d hybrid promoter (International application WO 96/41889) or else the XPR2 hybrid promoters described in Mazdak et al. (2000).

Terminator sequences which can be used in yeast are also well known to those skilled in the art. By way of example of terminator sequences which are usable in the method according to the invention, mention may be made of the terminator sequence of the PGK1 gene and the terminator sequence of the LIP2 gene, which are described in International application WO 01/83773.

The nucleotide sequence of the coding sequences of the heterologous genes can be optimized for its expression in yeast by methods well known to those skilled in the art (for review see Hedfalk, 2012).

The overexpression of endogenous enzyme can be obtained by replacing the sequences controlling the expression of said endogenous enzyme with regulatory sequences which allow a stronger expression, such as those described above. Those skilled in the art can thus replace the copy of the gene encoding an endogenous enzyme in the genome, and also its own regulatory sequences, by transformation of the mutant yeast strain with a linear polynucleotide comprising the open reading frame of the sequence encoding said endogenous enzyme under the control of regulatory sequences such as those described above. Advantageously, said polynucleotide is framed by sequences which are homologs of sequences located on each side of the chromosomal gene encoding said endogenous enzyme. Selectable markers can be inserted between the sequences ensuring recombination in order to make it possible, after transformation, to isolate the cells where the integration of the fragment has occurred by demonstration of the corresponding markers. Also advantageously, the promoter and terminator sequences used belong to genes different than the one encoding the endogenous enzyme to be overexpressed, so as to minimize the risks of unwanted recombination in the genome of the yeast strain.

The overexpression of an endogenous enzyme can also be obtained by introducing into the yeast strain according to the invention supernumerary copies of the gene encoding said endogenous enzyme under the control of regulatory sequences such as those described above. Said additional copies encoding said endogenous enzyme can be carried by an episomal vector, i.e. a vector capable of replicating in the yeast. Preferably, these additional copies are carried by an integrative vector, i.e. one which integrates at a given place in the genome of the yeast (Mazdak et al., 2004). In this case, the polynucleotide comprising the gene encoding said endogenous enzyme under the control of regulatory regions is integrated by targeted integration.

The targeted integration of a gene into the genome of a yeast is a molecular biology technique well known to those skilled in the art: a DNA fragment is cloned into an integrative vector, introduced into the cell to be transformed, said DNA fragment then integrates by homologous recombination into a targeted region of the recipient genome (Orr-Weaver et al., 1981). Methods for transforming yeasts are also well known to those skilled in the art and are described, in particular, by Ito et al. (1983), Klebe et al. (1983) and Gysler et al. (1990). Selectable markers can also be inserted between the sequences ensuring recombination in order to make it possible, after transformation, to isolate the cells where the integration of the fragment has occurred by demonstration of the corresponding markers.

Said additional copies can also be carried by PCR fragments, the ends of which are homologous to a given locus of the yeast, thus allowing the integration of said copies into the genome of the yeast by homologous recombination.

Said additional copies can also be carried by self-cloning vectors or PCR fragments, the ends of which have a zeta region absent from the genome of the yeast, thus allowing the integration of said copies into the genome of the yeast by random insertion as described in application US 2012/0034652.

Any gene transfer method known from the prior art can be used to introduce, into a yeast strain, a gene knock out cassette or to introduce a gene encoding an enzyme. Preferably, the method with lithium acetate and with polyethylene glycol, described by Gaillardin et al. (1987) and Le Dali et al. (1994), is used.

According to another advantageous embodiment of the method for obtaining a mutant oleaginous yeast strain capable of synthesizing ricinoleic acid according to the present invention, it also comprises the overexpression, in said yeast strain, of an enzyme capable of catalyzing the formation of triacylglycerol (TAG) from 1,2-sn-diacylglycerol.

This enzyme capable of catalyzing the formation of triacylglycerol (TAG) from 1,2-sn-diacylglycerol can be an acyl-CoA:diacylglycerol acyl transferase (DGAT; E.C. 2.3.1.20) or a phospholipid:diacylglycerol acyl transferase (PDAT; E.C. 2.3.1.158). This enzyme may be endogenous with respect to said yeast strain. Preferably, this enzyme is a PDAT, more preferably the endogenous PDAT of said yeast strain. PDAT makes it possible to transfer ricinoleic acid from the phospholipid to diacylglycerol.

According to another advantageous embodiment of the method for obtaining a mutant oleaginous yeast strain capable of synthesizing ricinoleic acid according to the present invention, it also comprises:

the overexpression of a monoacylglycerol acyl transferase, advantageously of a yeast monoacylglycerol acyl transferase, more advantageously of the endogenous monoacylglycerol acyl transferase of said strain (this method for obtaining a mutant oleaginous yeast strain and the yeast strain obtained by means of this method being particularly advantageous) and/or the overexpression of a patatin-like triacylglycerol lipase, advantageously of a yeast patatin-like triacylglycerol lipase, more advantageously the endogenous patatin-like triacylglycerol lipase of said strain and/or the inhibition of the expression or of the activity of the endogenous 2-methylcitrate dehydratase of said strain (this method for obtaining a mutant oleaginous yeast strain and the strain obtained by means of this method being particularly advantageous) and/or the overexpression of at least one of the two subunits of ATP citrate lyase, advantageously of at least one of the two subunits of yeast ATP citrate lyase, more advantageously of at least one of the two subunits of the endogenous ATP citrate lyase of said strain and/or the overexpression of a diacylglycerol:choline-O phosphotransferase, advantageously of a yeast diacylglycerol:choline-O phosphotransferase, more advantageously of the endogenous diacylglycerol:choline-O phosphotransferase of said strain (this method for obtaining a mutant oleaginous yeast strain and the strain obtained by means of this method being particularly advantageous) and/or the overexpression of an ethanolamine phosphotransferase, advantageously of a yeast ethanolamine phosphotransferase, more advantageously of the endogenous ethanolamine phosphotransferase of said strain and/or the overexpression of a phospholipase $A_2$, advantageously of a yeast phospholipase $A_2$, more advantageously of the endogenous phospholipase $A_2$ of said strain and/or the overexpression of an acyl-CoA:lysophosphatidylcholine acyl transferase, advantageously of a yeast acyl-CoA:lysophosphatidylcholine acyl transferase, more advantageously of an endogenous acyl-CoA:lysophosphatidylcholine acyl transferase of said strain and/or the overexpression of a cytochrome-$b_5$ reductase, advantageously of an endogenous cytochrome-$b_5$ reductase of said strain (this method for obtaining a mutant oleaginous yeast strain and the strain obtained by means of this method being particularly advantageous) and/or the overexpression of an inositol/phosphatidyl inositol phosphatase, advantageously of the endogenous inositol/phosphatidyl inositol phosphatase of said strain and/or the overexpression of an elongase, advantageously of an endogenous elongase of said strain.

The enzymes overexpressed in said yeast strain can come from any prokaryotic or eukaryotic organism. The coding sequence of the genes encoding these enzymes can be optimized for its expression in the yeast by methods well known to those skilled in the art (for review, see Hedfalk, 2012).

According to one advantageous arrangement of this embodiment, at least one of the enzymes overexpressed is endogenous with respect to said strain, preferably all the enzymes overexpressed are endogenous with respect to said strain.

In yeasts, the monoacylglycerol acyl transferase (MAGT; 1-acyl-sn-glycerol-3-phosphate acyl transferase; E.C. 2.3.1.51) is encoded by the SLC1 gene (Beopoulos et al., 2009 and 2012; International application WO 2012/001144). More particularly, the coding sequence of the SLC1 gene and the peptide sequence of the monoacylglycerol acyl transferase of *Y. lipolytica* CLIB122 are available in the Génolevures or GenBank databases under the following accession number or name: YALI0E18964g/YALI0E18964p.

In yeasts, the patatin-like triacylglycerol lipase (TGL5; triacylglycerol lipase; E.C. 3.1.1.3) is encoded by the TGL5 gene (Beopoulos et al., 2009 and 2012). More particularly, the coding sequence of the TGL5 gene and the peptide sequence of the patatin-like triacylglycerol lipase of *Y. lipolytica* CLIB122 are available in the Génolevures or GenBank databases under the following accession number or name: YALI0D16379g/YALI0D16379p.

In yeasts, 2-methylcitrate dehydratase (E.C. 4.2.1.79) is a mitochondrial protein which catalyzes the conversion of 2-methylcitrate into 2-methyl-cis-aconitate in the 2-methylcitrate cycle of propionate metabolism (Uchiyama et al., 1982; Tabuchi et al., 1981). It is encoded by the PHD1 gene. More particularly, the coding sequence of the PHD1 gene and the peptide sequence of the methylcitrate dehydratase of *Y. lipolytica* CLIB122 are available in the Génolevures or GenBank databases under the following accession number or name: YALI0F02497g YALI0F02497p.

In yeasts, the ATP citrate lyase (E.C. 2.3.3.8) consists of two subunits encoded by two genes (ACL1 and ACL2 respectively) (Beopoulos et al., 2009). The ATP citrate lyase of some oleaginous yeasts has been characterized by Boulton et al. (1981). More particularly, the coding sequence of the ACL1 and ACL2 genes and the peptide sequence of subunits A and B of the ATP citrate lyase of *Y. lipolytica* CLIB122 are available in the Génolevures or GenBank databases under the following accession numbers or names: ACL1/subunit A: YALI0E34793g/YALI0E347939p, and ACL2/subunit B: YALI0D24431 g/YALI0D24431p.

In yeasts, the diacylglycerol:choline-O phosphotransferase (E.C. 2.7.8.2) is encoded by the CPT1 gene. More particularly, the coding sequence of the CPT1 gene and the peptide sequence of the diacylglycerol:choline-O phosphotransferase of *Y. lipolytica* CLIB122 are available in the Génolevures or GenBank databases under the following accession number or name: YALI0E26565g/YALI0E26565p.

In yeasts, the ethanolamine phosphotransferase (EPT1; E.C. 2.7.8.1) is encoded by the EPT1 gene. More particularly, the coding sequence of the EPT1 gene and the peptide sequence of the ethanolamine phosphotransferase of *Y. lipolytica* CLIB122 are available in the Génolevures or GenBank databases under the following accession number or name: YALI0C10989g/YALI0C10989p.

In yeasts, the phospholipase $A_2$ (PLA2; E.C. 3.1.1.3; 3.1.1.13; 3.1.1.4 and 2.3.1.51) is encoded by the LPA1 gene. More particularly, the coding sequence of the LPA1 gene and the peptide sequence of the phospholipase $A_2$ of *Y. lipolytica* CLIB122 are available in the Génolevures or GenBank databases under the following accession number or name: YALI0F10010g/YALI0F10010p.

In yeasts, the acyl-CoA:lysophosphatidylcholine acyl transferases (LPCAT; (E.C. 2.3.1.51; 2.3.1.23; 2.3.1.-) are encoded by 3 genes, respectively LCA1, LCA2 and LCA3. More particularly, the coding sequence of the LCA1, LCA2 and LCA3 genes and the peptide sequence of the acyl-CoA:lysophosphatidylcholine acyl transferases 1, 2 and 3 of *Y. lipolytica* CLIB122 are available in the Génolevures or GenBank databases under the following accession numbers or names: LCA1: YALI0F19514g/YALI0F19514p; LCA2: YALI0C20625g/YALI0C20625p and LCA3: YALI0C14036g/YALI0C14036p.

In yeasts, the cytochrome-$b_5$ reductases (E.C. 1.6.2.2) are encoded by two genes, respectively MCR1 and CBR1 (Sickmann et al., 2003; Dujon et al., 2004). More particularly, the coding sequence of the MCR1 and CBR1 genes and peptide sequence of the cytochrome-$b_5$ reductases of *Y. lipolytica* CLIB122 are available in the Génolevures or GenBank databases under the following accession numbers or names: MCR1: YALI0D1330g/YALI0D1330p and CBR1: YALI0D04983g/YALI0D04983p.

In yeasts, the inositol/phosphatidyl inositol phosphatase (E.C. 3.1.3.-) is encoded by the SAC1 gene (Whitters et al., 1993). More particularly, the coding sequence of the SAC1 gene and the peptide sequence of the inositol/phosphatidyl inositol phosphatase of *Y. lipolytica* CLIB122 are available in the Génolevures or GenBank databases under the following accession number or name: YALI0D05995g/YALI0D05995p.

In yeasts, the elongases (E.C. 2.3.1.199) are encoded by two genes, respectively ELO1 and ELO2. More particularly, the coding sequence of the ELO1 and ELO2 genes and the peptide sequences of the elongases A and B respectively of *Y lipolytica* CLIB122 are available in the Génolevures or GenBank databases under the following accession numbers or names: ELO1: YALI0F06754g, and ELO2: YALI0B20196g.

According to another preferred embodiment of the method for obtaining a mutant oleaginous yeast strain capable of synthesizing an unusual omega-9 fatty acid according to the present invention, the unusual omega-9 fatty acid is vernolic acid and said method comprises the expression, in said strain, of a heterologous enzyme having an oleate (Δ12) epoxidase activity.

According to one advantageous arrangement of this embodiment, the oleate (Δ12) epoxidase is that of *Crepis alpina, Crepis palaestina* or *Vernonia galamensis* (Lee et al., 1998).

A subject of the present invention is also:
- a mutant oleaginous yeast strain which is of use as a template yeast strain for obtaining other mutant oleaginous yeast strains, capable of being obtained by means of a method according to the present invention defined above, and
- a mutant oleaginous yeast strain capable of synthesizing an unusual omega-9 fatty acid, preferably capable of producing ricinoleic acid or vernolic acid, more preferably ricinoleic acid, capable of being obtained by means of a method according to the present invention defined above.

By way of example of mutant oleaginous yeast strains which are of use as template yeast strains for obtaining other mutant oleaginous yeast strains, mention may be made of those having the genotype:

pox1-6Δ dga1Δ lro1Δ dga2Δ fad2Δ or
ura3-302 leu2-270 xpr2-322 pox1-6Δ dga1Δ lro1Δ dga2Δ fad2Δ.

By way of example of mutant oleaginous yeast strains capable of synthesizing ricinoleic acid, mention may be made of those having the genotype:

pox1-6Δ dga1Δ lro1Δ dga2Δ fad2Δ pTEF-CpFAH12
pox1-6Δ dga1Δ lro1Δ dga2Δ fad2Δ pTEF-CpFAH12x2 pTEF-LRO1
pox1-6Δ dga1Δ lro1Δ dga2Δ fad2Δ pTEF-CpFAH12x3 pTEF-LRO1x2
pox1-6Δ dga1Δ lro1Δ dga2Δ fad2Δ pTEF-CpFAH12x2 pTEF-LRO1 pTEF-cpFAH12 pTef-LRO1
pox1-6Δ dga1Δ lro1Δ dga2Δ fad2Δ pTEF-CpFAH12x2 pTEF-LRO1 pTEF-ACL1
pox1-6Δ dga1Δ lro1Δ dga2Δ fad2Δ pTEF-CpFAH12x2 pTEF-LRO1 pTEF-ACL2
pox1-6Δ dga1Δ lro1Δ dga2Δ fad2Δ pTEF-CpFAH12x2 pTEF-LRO1 phd1Δ
pox1-6Δ dga1Δ lro1Δ dga2Δ fad2Δ pTEF-CpFAH12x2 pTEF-LRO1 pTEF-SLC1
pox1-6Δ dga1Δ lro1Δ dga2Δ fad2Δ pTEF-CpFAH12x2 pTEF-LRO1 pTEF-SAC1
pox1-6Δ dga1Δ lro1Δ dga2Δ fad2Δ pTEF-CpFAH12x2 pTEF-LRO1 pTEF-LRO2
pox1-6Δ dga1Δ lro1Δ dga2Δ fad2Δ pTEF-CpFAH12x2 pTEF-LRO1 pTEF-TGL5
pox1-6Δ dga1Δ lro1Δ dga2Δ fad2Δ pTEF-CpFAH12x2 pTEF-LRO1 pTEF-MCR1
pox1-6Δ dga1Δ lro1Δ dga2Δ fad2Δ pTEF-CpFAH12x2 pTEF-LRO1 pTEF-LCA1
pox1-6Δ dga1Δ lro1Δ dga2Δ fad2Δ pTEF-CpFAH12x2 pTEF-LRO1 pTEF-LCA2
pox1-6Δ dga1Δ lro1Δ dga2Δ fad2Δ pTEF-CpFAH12x2 pTEF-LRO1 pTEF-LCA3
pox1-6Δ dga1Δ lro1Δ dga2Δ fad2Δ pTEF-CpFAH12x2 pTEF-LRO1 pTEF-LPA1
pox1-6Δ dga1Δ lro1Δ dga2Δ fad2Δ pTEF-CpFAH12x2 pTEF-LRO1 pTEF-CPT1
pox1-6Δ dga1Δ lro1Δ dga2Δ fad2Δ pTEF-CpFAH12x2 pTEF-LRO1 pTEF-EPT1
pox1-6Δ dga1Δ lro1Δ dga2Δ fad2Δ pTEF-CpFAH12x2 pTEF-LRO1 pTEF-ELOA
pox1-6Δ dga1Δ lro1Δ dga2Δ fad2Δ pTEF-CpFAH12x2 pTEF-LRO1 pTEF-ELOB
pox1-6Δ dga1Δ lro1Δ dga2Δ fad2Δ pTEF-CpFAH12x3 pTEF-LRO1x2 pTEF-MCR1
pox1-6Δ dga1Δ lro1Δ dga2Δ fad2Δ pTEF-CpFAH12x3 pTEF-LRO1x2 pTEF-LCA1

Advantageously, these mutant oleaginous yeast strains capable of synthesizing an unusual omega-9 fatty acid, such as ricinoleic acid or vernolic acid, are also capable of secreting said unusual omega-9 fatty acid.

A subject of the present invention is also the use of a mutant oleaginous yeast strain capable of synthesizing an unusual omega-9 fatty acid according to the present invention as defined above, for producing an omega-9 fatty acid. Said omega-9 fatty acid is preferably ricinoleic acid or vernolic acid, more preferably ricinoleic acid.

A subject of the present invention is also a method for producing omega-9 fatty acid, comprising a step of culturing, on an appropriate medium, a mutant oleaginous yeast strain capable of synthesizing an unusual omega-9 fatty acid according to the present invention as defined above. Said omega-9 fatty acid is preferably ricinoleic acid or vernolic acid, more preferably ricinoleic acid.

Said method for producing omega-9 fatty acid comprises a first step of culturing said mutant oleaginous yeast strain according to the present invention in an appropriate medium and a second step of harvesting the omega-9 fatty acids produced by the culturing in step 1.

Said appropriate medium may comprise various carbon-based sources for growth, such as, for example, glucose, sucrose or glycerol. Complex sources for providing this carbon-based substrate may also be used, such as molasses. It may also comprise vegetable oils or oleic acid as bioconversion substrate. Said appropriate medium may be a rich medium based on yeast extract, on tryptone or on peptone (for example 5 g/l yeast extract-50 g/l glucose), or a conventional minimal medium, as described by Mlickova et al. (2004) or a medium optimized for said yeast (International application WO 2007/144445; Emond et al., 2010) comprising trace elements, iron and vitamins and also ortho-phosphoric acid and ammonia or any other nitrogen source known to those skilled in the art.

The culture media and the methods for culturing the oleaginous yeasts are well known to those skilled in the art.

The culturing of the oleaginous yeasts can be carried out in a fermentor.

The present invention will be understood more clearly by means of the additional description which will follow, which refers to the obtaining of a mutant template *Y. lipolytica* yeast strain according to the present invention and of mutant *Y. lipolytica* yeast strains capable of synthesizing ricinoleic acid, and also of the appended figures:

FIG. 1: table describing the plasmids and the *E. coli* and *Y. lipolytica* strains used to obtain the mutant *Y. lipolytica* strains according to the present invention.

FIG. 2: diagrammatic representation of the construction of the mutant *Y. lipolytica* strains according to the present invention and their genotype.

FIG. 3: pairs of primers used for cloning the genes of interest.

FIG. 4: fatty acid composition (percentages relative to the total fatty acids) of mutant yeast strains (A) expressing the oleate hydroxylase of *R. communis* (RcFAH12) or of *C. purpurea* (CpFAH12) in various genetic backgrounds and (B) coexpressing RcFAH12 or CpHAH12 and the oleate desaturase of *R. communis* (RcDGAT2), of *C. purpurea* (CpDGAT2) or of *Y. lipolytica* (YlLRO1) in various genetic backgrounds.

Figure 5:
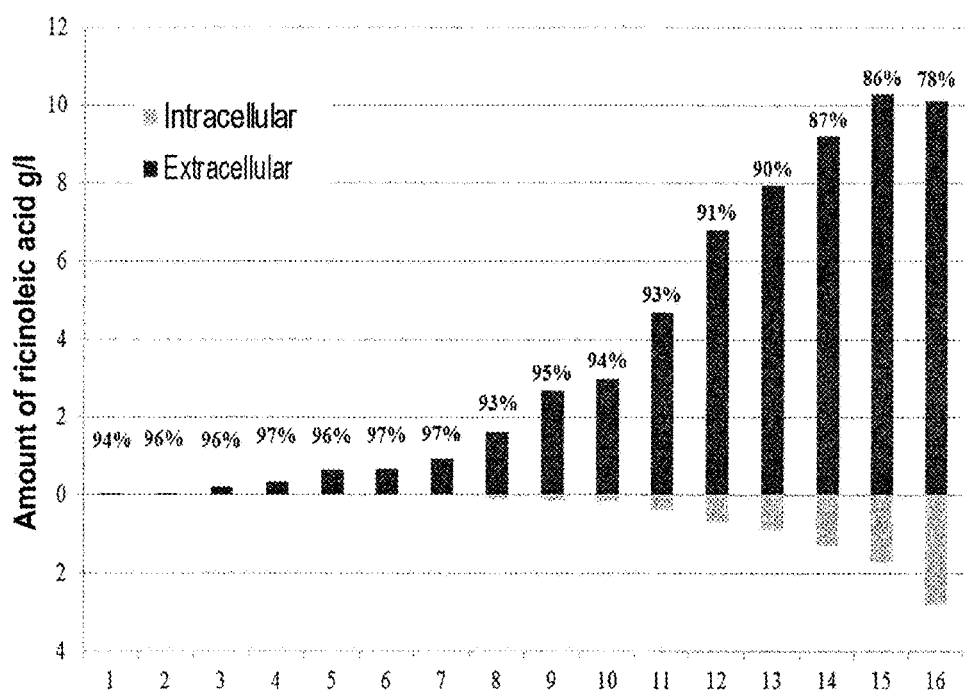

FIG. 5: evolution of the amount (in g/l of culture) of ricinoleic acid produced during the fermentation by the JMY3030 strain. The extracellular amount of ricinoleic acid is represented in black. The intracellular amount of ricinoleic acid is represented in gray. The label above gives the % of extracellular ricinoleic acid.

FIG. 6: sequence of the primers used for the cloning of the genes involved in the lipid metabolism of *Y. lipolytica*. The forward (for) primers contain a BamHI site, the reverse (rev) primers contain an AvrII site. The sited introduced are underlined. The internal BamHI sites in the ACL2 gene were removed by modifying a base (in bold) at the BamHI site. The BamHI, mutated BamHI and AvrII sites are underlined.

Figure 7:
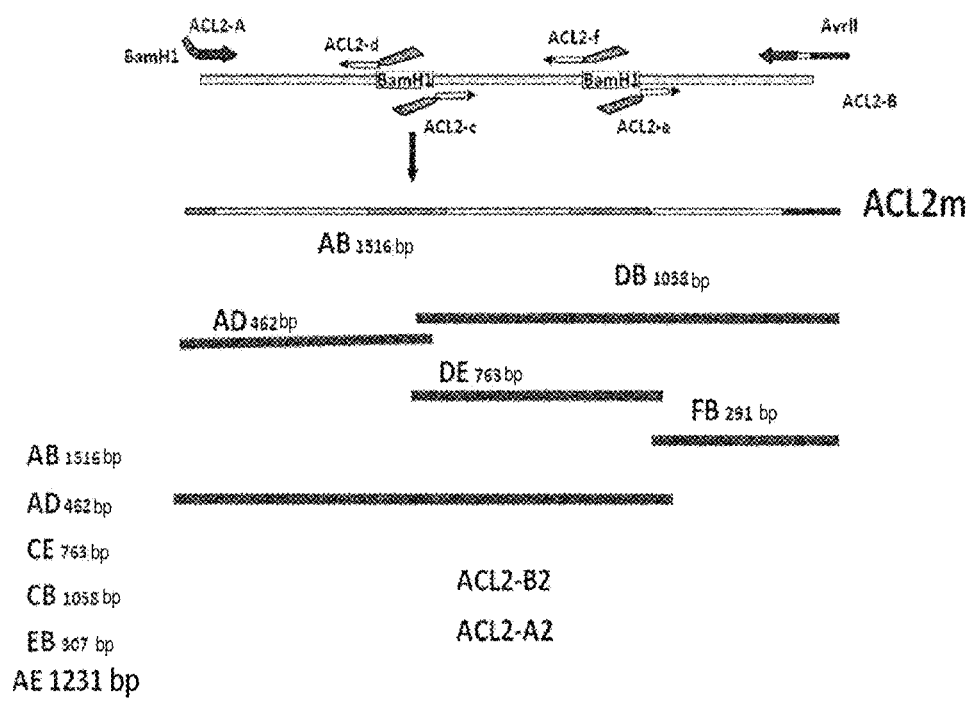

FIG. 7: diagram of the strategy adopted for amplifying the *Y. lipolytica* ACL2 gene while eliminating the two BamHI restriction sites.

FIG. 8A and FIG. 8B: diagrammatic representation of the construction of the mutant *Y. lipolytica* strains from the JMY2853 strain (FIG. 8A) and the JMY3431 strain (FIG. 8B) according to the present invention and their genotype.

FIG. 9A and FIG. 9B: (FIG. 9A) mutant *Y. lipolytica* yeast strains obtained from the JMY2853 (Ura$^-$, Leu$^-$) strain by overexpression or deletion of a target gene. The results of the genetic modifications on ricinoleic acid production are represented as percentage relative to the JMY2556 strain. The JMY2556 (Ura$^+$, Leu$^-$) strain was used as control since it has the same auxotrophies as the constructed strains. (FIG. 9B) mutant *Y. lipolytica* yeast strains obtained from the JMY3431 (Ura$^-$, Leu$^-$) strain by overexpression of a target gene. The results of the genetic modifications on the ricinoleic acid production are represented as percentage relative to the JMY3030 strain. *+: overexpression; −: deletion.

Figure 10A:
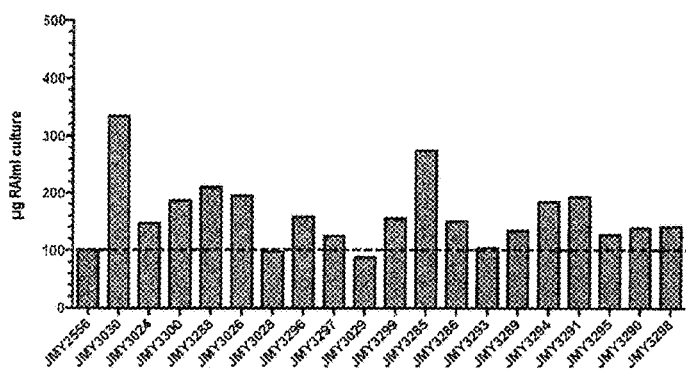
Figure 10B:
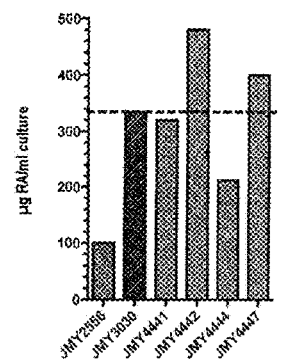

FIG. 10A and FIG. 10B: comparison of the amount (in µg/ml of culture) of ricinoleic acid produced by neosynthesis by the strains deriving from the JMY2556 strain (FIG. 10A) and by the strains deriving from the JMY3431 (JMY3030) strain (FIG. 10B).

Figure 11A:
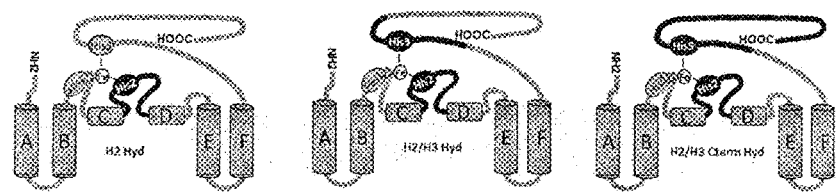
Figure 11B:
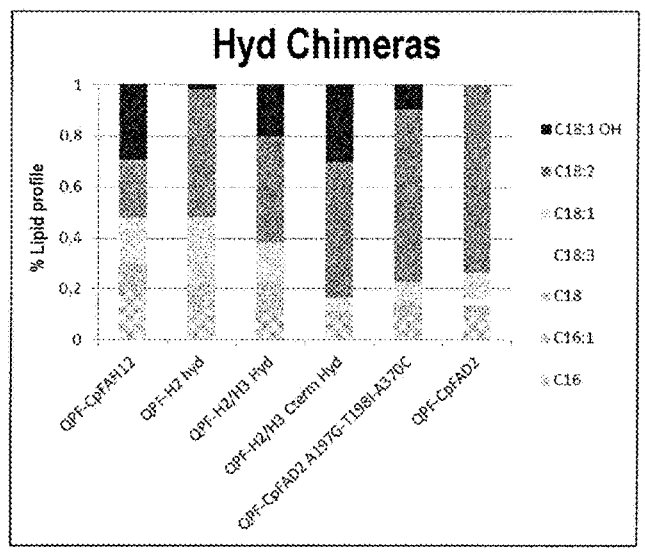

FIG. 11A and FIG. 11B: (FIG. 11A) diagrammatic representation of various proteins which are chimeric between a desaturase (in gray) and a hydroxylase (in black). (FIG. 11B) lipid composition of various strains after 96 h of culture in a flask containing 5% of glucose (YEDs) for the mutant yeast strains QPF-CpFAH12, QPF-H2_hyd, QPF-H2/H3_hyd and QPF-H2/H3_hyd Cterm.

EXAMPLE I: OBTAINING AND CHARACTERIZATION OF A MUTANT TEMPLATE *Y. LIPOLYTICA* YEAST STRAIN FOR OBTAINING OTHER MUTANT YEAST STRAINS; MUTANT YEAST STRAINS OBTAINED FROM SAID TEMPLATE YEAST STRAIN AND CAPABLE OF SYNTHESIZING RICINOLEIC ACID

1) Materials and Methods i) Strains and Media

The mutant *Y. lipolytica* strains are derived from the auxotrophic *Y. lipolytica* strain Pold (Leu$^-$ Ura$^-$; CLIB 139; of genotype MatA Ura3-302, Leu2-270, xpr2-322), itself derived from the wild-type *Y. lipolytica* strain W29 (of genotype MatA; ATCC 20460) by genetic modification. The Pold and W29 strains were described by Barth and Gaillardin (1996). The strains used to obtain the strains according to the present invention are presented in the table of FIG. 1. Their construction is represented in FIG. 2 and described in detail below.

The *Y. lipolytica* media and culture conditions were described by Barth and Gaillardin (1996). A rich medium (YPD), a minimum medium+glucose (YNB) and a minimum medium+casamino acids (YNBcasa) or uracil (YNBura) were prepared as described by Mlickova et al. (2004). The minimum medium (YNB) contains 0.17% (w/v) of yeast nitrogen base (without amino acid and ammonium sulfate, YNBww; Difco, Paris, France), 0.5% (w/v) of NH$_4$Cl, 0.1% (w/v) of yeast extract (Bacto-DB) and 50 mM of phosphate buffer (pH 6.8). The glucose medium for the neosynthesis of ricinoleic acid (YED$_5$) contains 1% (w/v) of yeast extract (Bacto-DB) and 5% (w/v) of glucose.

The *Escherichia coli* strain Mach1-T1 (Invitrogen) was used for the transformation and the amplification of the recombinant plasmid DNA. The cells were cultured on an LB medium (Sambrook et al., 1989). Kanamycin (40 µg/ml) was used to select the plasmids.

ii) General Molecular Biology Techniques

Standard molecular biology techniques, well known to those skilled in the art, were used. The restriction enzymes were obtained from New England Biolabs (Evry, France). The genomic DNA of the yeast transformants was obtained as described by Querol et al. (1992). A thermal cycler (Applied Biosystems 2720) and the Taq (Takara, Shiga, Japan) and Pyrobest (Takara, Shiga, Japan) DNA polymerases were used for the PCR amplification. The fragments amplified were purified with the QIAgen purification kit (Qiagen, Hilden, Germany) and the digested DNA fragments were recovered from agarose gels with the QIAquick gel extraction kit (Qiagen). The set of Staden programs (Dear and Staden, 1991) was used for the sequence analysis. The transformation of the yeast cells was carried out by the lithium acetate method (Gaillardin et al., 1985).

iii) Construction of Disrupted *Y. lipolytica* Strains and Excision of the Marker The deletion cassettes were produced by PCR amplification as described by Fickers et al. (2003) using the pairs of primers described by Beopoulos et al. (2008 and 2012) and in FIG. 3. The PT cassettes (see Fickers et al., 2003) were then inserted into the PCR4$^R$Blunt-TOPO vector (Life Technologies, Carlsbad, Calif.) and the auxotrophic marker (URA3 or LEU2) was then inserted by cloning at the Iscel site of the vectors so as to generate the corresponding JME vectors (PUT or PLT) (see FIG. 1). The PUT and PLT disruption cassettes were introduced into the *Y. lipolytica* genome by transformation using the lithium acetate method. The Ura+ and Leu+ transformants were selected on the YNBcasa and YNBura media, respectively. The corresponding ylΔ12-ver1 and ylΔ12-ver2 primers (see FIG. 3) were used to verify the disruption of the gene by PCR amplification of the genomic loci. The markers were excised using the Cre-lox recombinase system by transformation with the pUB4-Crel replicative plasmid (JME547) as described by Fickers et al. (2003). The strains were then cleared of the plasmid by successive replications on rich medium.

iv) Cloning and Expression of the Heterologous Hydroxylases and Acyl Transferases Under the Control of the TEF Constitutive Promoter The genes of interest were placed under the control of the TEF constitutive promoter of *Yarrowia lipolytica* (Muller et al., 1998). The codons of the heterologous genes encoding a hydroxylase and an acyl transferase were optimized for expression in the yeast and synthesized by Genscript (New Jersey, USA). The encoding genes were then inserted between the BamHI and AvrII restriction sites of the expression vector derived from JMP62 containing the pTEF promoter and the URA3ex selectable marker (JME1046) described by Nicaud et al. (2002). The JMP62 vectors containing the LEU2ex selectable marker were obtained by replacement of the marker using the IsceI restriction site upstream/downstream of URA3ex in the JME802 vector (Fickers et al., 2003; Nicaud et al., 2002). The plasmids were digested with NotI prior to transformation. The transformants were selected by auxotrophy on the appropriate minimal medium.

v) Lipid Analysis

The lipids of the equivalent of 10 OD units of lyophilized cells in culture were extracted using the procedure described by Folch et al. (1957) for the TLC (thin layer chromatography) analysis or were directly converted into their methyl esters for the GC analysis, as described by Browse et al. (1986). The GC analysis of the fatty acid methyl esters (FAMEs) was carried out on a gas chromatograph (Varian 3900) equipped with a flame ionization detector and a Varian FactorFour vf-23 ms column, with a washing specification at 260° C. of 3 pA (30 m, 0.25 mm, 0.25 µm). The fatty acids (FAs) were identified by comparison with the commercial standard fatty acid methyl esters (FAME32, Supelco; methyl ricinoleate, Sigma) and quantified using the internal standard method with the addition of 50 g of commercial C17:0 (Sigma).

The analysis of the culture supernatants was carried out as follows: one volume of culture is mixed with one volume of isopropanol, centrifuged (1 minute, 13 000 rpm) and filtered on 0.2µ. Twenty microliters of the mixture are injected into HPLC with UV 254 nm detection on a C18 reverse-phase column (5 µm C18(2) 100 Å, LC Column 151×4.6 mm, Ea) at 40° C. with a 90/10/0.3 methanol/water/trifluoroacetic acid mixture as eluent at 1 ml/min.

vi) Lipid Analysis by Thin Layer Chromatography (TLC)

Pre-coated TLC plates (G60 silica, 20×20 cm, 0.25 mm thick) from Merck (Germany) were used. The lipid classes were separated with the 80/20/1 (v/v/v) hexane/ethyl ether/acetic acid solvent. For the visualization, the plates were sprayed with 1% of sulfuric vanillin in ethanol and incubated at 105° C. for 10 min. The various lipid classes were identified using commercial standards (Nu-chek, USA).

2) Results i) Comparison of the Heterologous Expression of the Oleate Hydroxylases of *Claviceps Purpurea* (CpFAH12) and of *Ricinus communis* (RcFAH12) for the Production of Ricinoleic Acid In order to evaluate the enzymatic capacities of the plant (*R. communis*) and fungus (*C. purpurea*) oleate (Δ12) hydroxylases to synthesize hydroxylated fatty acids in *Y. lipolytica*, the genes encoding RcFAH12 and CpFAH12 were expressed independently of one another, under pTEF strong constitutive promoter, in various genetic backgrounds of *Y. lipolytica*.

The coding sequences of RcFAH12 and CpFAH12 were optimized for expression thereof in the yeast (SEQ ID No. 21 and 22 respectively).

In order to avoid the conversion of oleic acid to linoleic acid by the endogenous desaturase of *Y. lipolytica*, the *Y. lipolytica* gene encoding the endogenous Δ12 desaturase (FAD2; YALI0B10153g) was deleted before the heterologous expression of the oleate hydroxylases. This deletion was carried out both in the Po1d strain and the JMY1233 strain (pox1-6Δ). The mutants obtained, called JMY1366 and JMY1762 respectively, were incapable of synthesizing linoleic acid.

The JMY2159 strain grouping together the deletions knocking out β-oxidation (pox1-6Δ), TAG synthesis (dga1Δ dga2Δ lro1Δ) and Δ12 desaturation (fad2Δ) is called PQF for simplification.

The cultures were carried out in batch mode on a medium containing glucose (YED$_5$), promoting lipid neosynthesis.

As shown by FIG. 4A, the fad2Δ mutants expressing the hydroxylase of the castor oil plant (RcFAH12) succeeded in synthesizing and accumulating ricinoleic acid at only 0.3% of its total lipids, independently of their ability to carry out B-oxidation (JMY1760 and JMY1763 strains). The mutant strain deleted of the TAG acyl transferases expressing RcFAH12 (JMY2331) contains 7% of ricinoleic acid, thereby suggesting that the absence of enzymatic activity in the previous constructs is to a large extent due to the unavailability of the substrate (oleic acid esterified to TAG). The homologous construct expressing CpFAH12 (JMY2324) contained up to 29% of ricinoleic acid (FIG. 4A). These results demonstrate that the fungal enzyme is more effective in *Y. lipolytica* than the plant enzyme.

In addition, all the strains tested were capable of synthesizing linoleic acid (C18:2), owing to the well-known potential of oleate hydroxylase enzymes to possess a bifunctional hydroxylation/desaturation activity. In the strains expressing RcFAH12, the linoleic acid amounted to 0.5% of the total lipids, whereas for the strains expressing CpFAH12, this percentage amounted to 15% of the total lipids. The ratio of hydroxylation to desaturation activity appears to be not only species-specific, but is also linked to the enzymatic activity. It was 10:1 for the PQF-RcFAH12 strain (JMY2331) and 2:1 for the PQF-CpFAH12 strain (JMY2324).

ii) Improvement in Ricinoleic Acid Production: Increase in the Number of Copies of the Hydroxylases and Coexpression with Acyl Transferases Specific for Ricinoleic Acid The expression of an additional copy of the CpFAH12 hydroxylase in the same genetic context (JMY2511) made it possible to obtain a mutant strain producing ricinoleic acid in an amount of 35% of its total lipids (FIG. 4B). These results demonstrate that the efficiency of the hydroxylation is associated with the number of copies expressed. In addition, for the strains expressing CpFAH12, the percentage of linoleic acid amounts to 15% and 21% of the total lipids depending on single or double overexpression of CpFAH12 respectively (JMY2324 and JMY2511 strains). Here also, the ratio of hydroxylation to desaturation activity does not only appear to be species-specific, but is also linked to the enzymatic activity. It was 2:1 for the PQF-CpFAH12 strain (JMY2324) and 1.5:1 for the PQF-CpFAH12x2 strain (JMY2511). However, the fraction of unsaturated C18 fatty acids (oleic acid, linoleic acid and ricinoleic acid) remained constant and represented approximately 70% of the total lipids for all the strains tested. In terms of lipid accumulation, the fad2-RcFAH12 strain (JMY1760) accumulated lipids up to 4% of its dry weight, whereas, for the pox1-6Δfad2Δ-RcFAH12 strain (JMY1763) the lipid accumulation reached 7% of the dry weight. All the PQF-derived strains accumulated lipids at approximately 5% of the dry weight.

In order to determine whether the level of ricinoleic acid synthesis is linked to the accumulation capacity of the yeast strains, the acyl transferase specific for ricinoleic acid, DGAT2 of *R. communis* (RcDGAT2) and of *C. purpurea* (CpDGAT2) respectively, was independently expressed, under the control of the pTEF promoter, in the PQF-CpFAH12 strain. The coding sequences of RcDGAT2 and CpDGAT2 were optimized for expression thereof in the yeast (SEQ ID No. 23 and 24 respectively). The native acyl transferase YlLRO1, which uses the sn-2 group of phospholipids where the hydroxylation occurs as the acyl donor for the TAG esterification, was also overexpressed in the PQF-CpFAH12 strain. The fatty acid composition of the mutants expressing the acyl transferase is presented in FIG. 4B. A significant decrease of 2 times the ricinoleic acid level was observed in the strain coexpressing CpFAH12-RcDGAT2 (JMY2329), in comparison with the parent strain expressing the hydroxylase of *C. purpurea* (JMY2324), accumulating ricinoleic acid at only 14% of the total lipids. The two strains accumulated lipids up to 5% of their dry weight, demonstrating the considerable decrease in the amount of ricinoleic acid produced when the DGAT2 acyl transferase of *R. communis* is expressed. In the strain coexpressing FAH12/DGAT2 of *C. purpurea* (JMY2517), only 5% of ricinoleic acid was detected (approximately 5% of the total lipids). With regard to the strain coexpressing FAH12/DGAT2 of *R. communis* (JMY2235), the RA accumulation was 2.5% of the total lipids (approximately 5% of total lipids), which corresponds to a 3-fold decrease compared with the parental strain not expressing RcDGAT2 (JMY2231). All the strains expressing DGAT were, however, capable of forming TAG, although ricinoleic acid was not detected in this fraction. These results demonstrate that the specificity with respect to ricinoleic acid of the DGATs of *R. communis* and *C. purpurea* is modified when they are expressed in *Y. lipolytica*. Nevertheless, the CpFAH12 strain overexpressing the native LRO1 acyl transferase of *Y. lipolytica* (JMY2556 [Ura+, Leu−] or JMY2853 [Ura−, Leu−], the number of the strain varying according to the auxotrophies) accumulated ricinoleic acid up to 42% of its total lipids, with a fraction representing 20% of the total ricinoleic acid, esterified to TAG. This corresponds to an increase of 1.4-fold in the accumulation of ricinoleic acid compared with the parental strain (JMY2511). The lipid accumulation reached 13% of the dry weight of the cells, corresponding to an increase of 2.5-fold compared with the strains not expressing LRO1. The amount of ricinoleic acid produced reached 700 µg/ml (or 63 mg/g of dry weight). In agreement with the preceding results, in all the strains tested, the oleate hydroxylase is capable of continuing the hydroxylation reaction following the formation of linoleic acid (22%), but with a hydroxylation-to-desaturation ratio amounting to 2:1.

The JMY2853 strain was used as a template yeast strain for the multicopy overexpression of the genes encoding the CpFAH12 and YlLRO1 enzymes. A strain comprising 3 copies of CpFAH12 and 2 copies of the YlLRO1 acyl transferase was obtained (JMY3030 strain). It produces up to 53% of ricinoleic acid by neosynthesis on a glucose medium.

EXAMPLE II: PRODUCTION OF RICINOLEIC ACID BY THE *Y. LIPOLYTICA* YEAST STRAIN JMY3030 IN A FERMENTOR IN FED-BATCH MODE

The JMY3030 strain (containing 3 copies of CpFAH12 and 2 copies of YlLRO1) was used in a 10 l fermentor (4 l of liquid volume). The culture conditions are perfectly controlled in the fermentor (regulation of pH, of temperature and of aeration). The amount of biomass and therefore of producer cells is then improved, thereby making it possible to increase the ricinoleic acid production.

The fermentation was carried out in fed-batch mode, with glucose as carbon source for the growth and oleic acid as bioconversion substrate.

The culture was carried out on the minimal medium optimized for *Yarrowia lipolytica* (synthetic), with the addition of trace elements, iron and vitamins, as described in International application WO 2007/144445, with 160 g/l of glucose and 24 g/l of oleic acid in total and a pH regulated at 6 with ortho-phosphoric acid and ammonia.

The culture was inoculated at a biomass concentration of 0.48 g/l and the average growth rate was 0.19 $h^{-1}$. The cell concentration reached 90 $g_{cdw}$/l. Four controlled additions of oleic acid were carried out, first by addition of an emulsion of oleic acid at 20% (v/v), then of nonemulsified oleic acid (80% pure).

The final concentration of ricinoleic acid produced is 12 g/l, with a purity of 60% with respect to the total lipids.

The ricinoleic acid is secreted into the culture medium; the percentage in the supernatant is higher at the beginning of culture (where close to 95% of the ricinoleic acid is found in the supernatant portion) than at the end of culture, where it remains predominant in the supernatant, but its proportion decreases to 78% (see FIG. 5).

EXAMPLE III: GENETIC MODIFICATIONS OF THE *Y. LIPOLYTICA* YEAST STRAIN JMY2853 (JMY2556) IN ORDER TO INCREASE ITS RICINOLEIC ACID PRODUCTION

Genes capable of increasing the neosynthesis of ricinoleic acid were also identified. These novel target genes were the subject of novel constructions of strains on the basis of the JMY2853 template strain.

The insertion of the genes of interest into the JMP62-Ura3ex-pTEF vector is carried out by amplification of the genes with the primers described in FIG. 6, into which the sequences of the BamHI and AvrII restriction enzymes were introduced at the 5' and 3' ends respectively. The plasmids and the PCR products are digested with the enzymes and ligated to obtain the expression vectors.

For the YlACL2 gene which contains two BamHI restriction sites, mutations were introduced making it possible to eliminate these sites (see FIG. 7).

The expression vectors were verified by sequencing.

The constructions of the other expression vectors containing the Phospholipase A2 (YALI0F10010g), TGL5 (YALI0D16379g), LCAT3 (YALI0C14036g) and LRO2 (YALI0E08206g) genes were carried out using synthetic genes directly synthesized and cloned (Eurofins).

Some mutant strains obtained provide significant results in the bioconversion of oleic acid to ricinoleic acid and in the accumulation of the lipids produced. Their construction is represented in FIG. 8A and the results of these mutant strains are presented in FIGS. 9A and 10A.

EXAMPLE IV: GENETIC MODIFICATIONS OF THE *Y. LIPOLYTICA* YEAST STRAIN JMY3431 (JMY3030) IN ORDER TO INCREASE ITS RICINOLEIC ACID PRODUCTION

The genes capable of increasing the neosynthesis of ricinoleic acid that were identified were the subject of novel constructions of strains on the basis of the JMY3431 template strain.

The insertion of the genes of interest into the JMP62-Ura3ex-pTEF vector is carried out by amplification of the genes with the primers described in FIG. 6, in which the sequences of the BamHI and AvrII restriction enzymes were introduced at the 5' and 3' ends respectively. The plasmids and the PCR products were digested with the enzymes and ligated to obtain the expression vectors.

The expression vectors were verified by sequencing.

Some mutant strains obtained provide significant results both in the bioconversion of oleic acid to ricinoleic acid and in the accumulation of the lipids produced. Their construction is represented in FIG. 8B and the results of these mutant strains are presented in FIGS. 9B and 10B.

EXAMPLE V: EVOLUTION OF THE OLEATE DESATURASE OF *Y. LIPOLYTICA* TO OLEATE HYDROXYLASE

In order to obtain a microorganism not containing genes originating from a different species, it was envisioned to convert the desaturase of *Y. lipolytica* into hydroxylase. Indeed, hydroxylases and desaturases are homologous enzymes which belong to the same protein family and which share a strong similarity, both in terms of their sequence and in terms of their function: both modify oleic acid (either by creating a desaturation or by creating a hydroxylation).

However, since the hydroxylase of *C. purpurea* and the desaturase of *Y. lipolytica* come from two different organisms, they share only 47% of identical amino acids. It was therefore chosen to work firstly with the desaturase of *C. purpurea* which has 86% of amino acids identical to those of its hydroxylase. Thus, the difference in function between the desaturase and hydroxylase of this fungus is contained in the 14% of divergent sequences between these two enzymes.

Chimeras between the desaturase of *C. purpurea* (CpFAD2) and the hydroxylase of *C. purpurea* (CpFAH12) were constructed and expressed in the pox1-6Δdga1Δlro1Δdga2Δfad2Δ strain (denoted QPF). The representation of these chimeric proteins is shown diagrammatically in FIG. 11A. The H2 (amino acids 189 to 233), H3 (358-434) and H3 Cterm (358-477) domains of the CpFAH12 hydroxylase were integrated into the desaturase (CpFAD2). These domains were identified as essential in the hydroxylation function of the protein. The peptide sequences corresponding to these chimeras are the sequences SEQ ID Nos. 49 (H2-hyd), 50 (H2/H3-hyd) and 51 (H2/H3-hyd Cterm).

In all the strains expressing these chimeras, ricinoleic acid production could be observed (see FIG. 11B), said production representing 2% of the fatty acids for the QPF-H2_hyd strain, 20% for the QPF-H2/H3_hyd strain, and 30% for the QPF-H2/H3_hyd Cterm strain. The latter strain makes it possible to again find a level of hydroxylation identical to that obtained with the strain expressing the CpFAH12 hydroxylase. (29% of hydroxylation).

A more thorough examination of the amino acid residues responsible for the hydroxylation function of the enzyme made it possible to more accurately identify the three positions in the hydroxylation function. A strain expressing a variant of the CpFAD2 desaturase combining only 3 mutations (CpFAD2 A197G, T198I, and A370C) makes it possible to obtain 10% of hydroxylation compared with 29% for the CpFAH12 hydroxylase.

REFERENCES

Bafor M. et al., 1991, Biochem J., 280:507-514
Barth G. and Gaillardin C., 1996 *Yarrowia lipolytica*, In Nonconventional yeasts in biotechnology, vol. 1, K. Wolf, K. D. Breunig, and G. Barth (ed.), Springer-Verlag, Berlin, Germany, 313-388
Beopoulos A. et al., 2008, Appl Environ Microbiol., 74:7779-7789
Beopoulos A. et al., 2009, Prog Lipid Res., 48:375-387
Beopoulos A. et al., 2011, Appl Microbiol Biotechnol., 90:1193-1206
Beopoulos A. et al., 2012, Appl Microbiol Biotechnol., 93:1523-1537
Berninger G. et al., 1993, Eur J Biochem., 216:607-613
Boulton C. A. et al., 1981, J Gen Microbiol., 127:169-176
Broadwater J. A. et al, 2002, J Biol Chem., 277:15613-15620
Broun P. and Somerville C., 1997, Plant Physiol., 113:933-942
Broun P. et al., 1998, Science, 282:1315-1317
Browse J. et al., 1986, Anal Biochem., 152:141-145
Burgal J. et al., 2008, Plant Biotechnol J., 6:819-831
Chan A. P. et al., 2010, Nat Biotechnol., 28:951-956
Dahlke B. et al., 1995, JAOCS, 72:349
Dear S and Staden R., 1991, Nucleic Acids Res., 19:3907-3911
Dujon B. et al., 2004, Nature, 430:35-44
Dulermo T. and Nicaud J.-M., 2011, Metab Eng., 13:482-491
Emond S. et al., 2010, Appl Environ Microbiol., 76:2684-2687
Einerhand A. W. et al., 1995, Mol Cell Biol., 15:3405-3414
Fickers P. et al., 2003, J Microbiol Methods, 55:727-737
Folch J. et al., 1957, J Biol Chem., 226:497-509
Gaillardin C. et al., 1985, Curr Genet. 10:49-58
Gaillardin C. et al., 1987, Curr Genet., 11:369-375
Gysler C. et al., 1990, Biotechn Techn., 4:285-290
Haddouche R. et al., 2011, Appl Microbiol Biotechnol., 91:1327-1340
Hedfalk K. (2012) 'Codon Optimisation for Heterologous Gene Expression in Yeast' in Springer Protocols: Methods in Molecular Biology. Recombinant protein production in yeast: methods and protocols. Volume 866 pp. 47-55. Springer Eds.
Holic R. et al., 2012, Appl Microbiol Biotechnol., 95:179-187
Ito H. et al., 1983, J Bacteriol., 153:163-168
Klebe R. J. et al., 1983, Gene, 25: 333-341
Knight B., 1979, Br Med J., 1:350-351
Kumar S. et al., 2012, Eukaryot Cell., 11:1083-1084
Le Dali M. T. et al., 1994, Curr Genet., 26:38-44
Lee M. et al., 1998, Science, 280:915-918
Lu C. et al., 2006, Plant J., 45:847-856
Luo Y. S. et al., 2000, Arch Biochem Biophys., 384:1-8
Luo Y. S. et al., 2002, Arch Biochem Biophys., 407:32-38
Mazdak et al., 2000, J Mol Microbiol Biotechnol., 2:207-216
Madzak C. et al., 2004, J Biotechnol., 109:63-81
Maftahi M. et al., Yeast, 1996, 12:859-868
Mavraganis I. et al., 2010, Appl Environ Microbiol 76:1135-1142
Meesapyodsuk D. et al., 2007, J Biol Chem., 143:959-969
Meesapyodsuk D. and Qiu X., 2008, Plant Physiol., 147:1325-1333
Mlickova K. et al., 2004, Appl Environ Microbiol., 70:3918-3924
Muller S. et al., 1998, Yeast, 14:1267-1283
Nicaud J.-M et al., 2002, FEMS Yeast Res., 2:371-379
Nicaud J.-M., 2012, Yeast, 29:409-418
Orr-Weaver T. L. et al., 1981, Proc. Natl. Acad. Sci. USA, 78:6354-6358
Papanikolaou S. et al., 2001, Antonie van Leeuwenhoek, 80:215-224
Papanikolaou S. et al., 2010, Eur J Lipid Sci Technol., 112:639-654
Papanikolaou S. et al., 2011a, Eur J Lipid Sci Technol., 113:1031-1051
Papanikolaou S. et al., 2011b, Eur J Lipid Sci Technol., 113:1052-1073
Papanikolaou S. et al., 2013, J Biotechnol., 168:303-314
Querol A. et al., 1992, Appl Environ Microbiol., 58:2948-2953
Rani S. H. et al., 2013, Microbiology, 159:155-166
Ratledge C. (1994). Yeasts, moulds, algae and bacteria as sources of lipids. Technological advances in improved and alternative sources of lipids. B. S. Kamel, Kakuda, Y. London, Blackie academic and professional: 235-291
Ratledge C., 2004, Biochimie, 86:807-815
Richard M. et al., 2001, J Bacteriol., 183:3098-3107

Sambrook J. et al., 1989, Molecular cloning: A laboratory manual. 2nd edn. Cold Spring Harbor Laboratory, Cold Spring Harbor, N.Y.

Schrader J. et al., 2004, Biotechnol Lett., 26:463-472

Sickmann A. et al., 2003, Proc Natl Acad Sci USA., 100: 13207-13212

Smith M. A. et al., 2003, Planta 217:507-516

Tabuchi T. et al., 1981, Agric Biol Chem., 45:2823-2829

Uchiyama H. et al., 1982, Eur J Biochem., 125:523-527

Wang H. et al., 1999a, Cell Biochem Biophys., 31:165-174

Wang H. J. et al., 1999b, J Bacteriol., 181:5140-5148

Whitters E. A. et al., 1993, J Cell Biol., 122:79-94

Yamamoto K. et al., 2008, Lipids, 43:457-460

Zhu Z. et al., 2012. Nat Commun., 3:1112-1122

---

The invention claimed is:

1. A method for obtaining a mutant oleaginous yeast strain, said method comprising the steps of:
   (a) providing an oleaginous yeast strain which comprises endogenous acyl-CoA:diacylglycerol acyl transferases, an endogenous acyl-CoA oxidase, an endogenous oleate desaturase, and optionally an endogenous phospholipid:diacylglycerol acyl transferase, and wherein fatty acid beta-oxidation occurs within the oleaginous yeast strain,
   (b) inhibiting the fatty acid beta-oxidation in said oleaginous yeast strain by inhibiting the expression or the activity of the endogenous acyl-CoA oxidase, of said strain, by deleting all or part of the gene encoding the endogenous acyl-CoA oxidase and/or inserting an exogenous sequence in the gene encoding the endogenous acyl-CoA oxidase,
   (c) inhibiting the expression or the activity of one or more of the endogenous acyl-CoA:diacylglycerol acyl transferases of said oleaginous yeast strain by deleting all or part of the gene encoding the one or more endogenous acyl-CoA:diacylglycerol acyl transferases and/or inserting an exogenous sequence in the gene encoding the one or more endogenous acyl-CoA:diacylglycerol acyl transferases,
   (d) inhibiting the expression or the activity of the endogenous oleate desaturase of said oleaginous yeast strain, by deleting all or part of the gene encoding the endogenous oleate desaturase and/or inserting an exogenous sequence in the gene encoding the endogenous oleate desaturase, and
   (e) expressing a heterologous enzyme having an oleate hydroxylase or oleate epoxidase activity in said oleaginous yeast strain, and
   (f) optionally inhibiting the expression or the activity of the endogenous phospholipid:diacylglycerol acyl transferase of said oleaginous yeast strain by deleting all or part of the gene encoding the endogenous phospholipid:diacylglycerol acyl transferase and/or inserting an exogenous sequence in the gene encoding the endogenous phospholipid:diacylglycerol acyl transferase;
   wherein the mutant oleaginous yeast strain is capable of synthesizing a fatty acid comprising a hydroxyl or epoxy group that is not produced in the oleaginous yeast strain prior to the modifications of (b) to (e).

2. The method of claim 1, wherein the fatty acid comprising a hydroxyl or epoxy group is an omega-9 fatty acid.

3. The method of claim 1, wherein the mutant oleaginous yeast strain belongs to a genus selected from the group consisting of *Candida, Cryptoccocus, Lipomyces, Rhodosporidium, Rhodotorula, Rhizopus, Trichosporon* and *Yarrowia*.

4. The method of claim 3, wherein the mutant oleaginous yeast strain is a mutant *Yarrowia lipolytica* strain.

5. The method of claim 2, wherein the omega-9 fatty acid is ricinoleic acid, and wherein the heterologous enzyme having an oleate hydroxylase activity is a heterologous enzyme having an oleate (Δ12) hydroxylase activity.

6. The method of claim 5, wherein the heterologous enzyme having an oleate (Δ12) hydroxylase activity is an oleate (Δ12) hydroxylase.

7. The method of claim 6, wherein the oleate (Δ12) hydroxylase is a *Ricinus communis* oleate (Δ12) hydroxylase (RcFAH12) or an oleate (Δ12) hydroxylase from a fungus of the ascomycetes division.

8. The method of in claim 7, wherein the oleate (Δ12) hydroxylase is an oleate (Δ12) hydroxylase from a fungus of the family Clavicipitaceae.

9. The method of claim 5, wherein the method further comprises overexpressing, in said oleaginous yeast strain, an enzyme capable of catalyzing the formation of triacylglycerol (TAG) from 1,2-sn-diacylglycerol, wherein the overexpression is obtained
   by placing one or more copies of a polynucleotide encoding the enzyme capable of catalyzing the formation of triacylglycerol (TAG) from 1,2-sn-diacylglycerol under the control of appropriate regulatory sequences comprising promoter sequences and/or terminator sequences,
   by replacing regulatory sequences controlling the expression of the enzyme capable of catalyzing the formation of triacylglycerol (TAG) from 1,2-sn-diacylglvcerol with regulatory sequences which allow a stronger expression and/or by transforming the oleaginous yeast strain with one or more copies of a gene encoding the enzyme capable of catalyzing the formation of triacylglycerol (TAG) from 1,2-sn-diacylglycerol.

10. The method of claim 9, wherein the enzyme capable of catalyzing the formation of TAG from 1,2-sn-diacylglycerol is a phospholipid:diacylglycerol acyl transferase (PDAT) of said oleaginous yeast strain.

11. The method of claim 1, wherein the method further comprises at least one of the following:
overexpressing a monoacylglycerol acyl transferase,
overexpressing a patatin-like triacylglycerol lipase,
inhibiting the expression or the activity of the endogenous 2-methylcitrate dehydratase of said oleaginous yeast strain by deleting all or part of the gene encoding the endogenous 2-methylcitrate dehydratase and/or inserting an exogenous sequence in the gene encoding the endogenous 2-methylcitrate dehydratase,
overexpressing at least one subunit of an ATP citrate lyase,
overexpressing a diacylglycerol:choline-O phosphotransferase,
overexpressing an ethanolamine phosphotransferase,
overexpressing a phospholipase A2,
overexpressing an acyl-CoA:lysophosphatidylcholine acyl transferase,
overexpressing a cytochrome-$b_5$ reductase,
overexpressing an inositol/phosphatidyl inositol phosphatase, and
overexpressing an elongase
wherein the overexpression of the monoacylglycerol acyl transferase, the patatin-like triacylglycerol lipase, the at least one subunit of an ATP citrate lyase, the diacylglycerol:choline-O phosphotransferase, the ethanolamine phosphotransferase, the phospholipase A2, the acylCoA:lysophosphatidylcholine acyl transferase, the cytochrome-$b_5$ reductase, the inositol/phosphatidyl inositol phosphatase, and the elongase is obtained by placing one or more copies of a polynucleotide encoding the enzymes to overexpress under the control of appropriate regulatory sequences comprising promoter sequences and/or terminator sequences, by replacing regulatory sequences controlling the expression of the enzyme to overexpress with regulatory sequences which allow a stronger expression, and/or by transforming the oleaginous yeast strain with one or more copies of a gene encoding the enzyme to overexpress.

12. The method of claim 11, wherein all the enzymes overexpressed are homologous with respect to said oleaginous yeast strain.

13. The method of claim 2, wherein the omega-9 fatty acid is vernolic acid, and wherein the heterologous enzyme having an oleate epoxidase activity is a heterologous enzyme having an oleate (Δ12) epoxidase activity.

14. A mutant oleaginous yeast strain obtained by the method of claim 1.

15. A method for producing an omega-9 fatty acid comprising a hydroxyl or epoxy group, said method comprising a step of culturing, on an appropriate medium, the mutant oleaginous yeast strain of claim 14 to thereby produce said omega-9 fatty acid comprising a hydroxyl or epoxy group.

16. The method of claim 15, wherein the omega-9 fatty acid comprising a hydroxyl or epoxy group is ricinoleic acid, and wherein the heterologous enzyme having an oleate hydroxylase activity is a heterologous enzyme having an oleate (Δ12) hydroxylase activity.

* * * * *